(12) United States Patent
Unger et al.

(10) Patent No.: US 9,801,959 B2
(45) Date of Patent: Oct. 31, 2017

(54) PHOSPHOLIPID COMPOSITION AND MICROBUBBLES AND EMULSIONS FORMED USING SAME

(71) Applicants: Evan C. Unger, Tucson, AZ (US); Daniel C. Evans, Tucson, AZ (US)

(72) Inventors: Evan C. Unger, Tucson, AZ (US); Daniel C. Evans, Tucson, AZ (US)

(73) Assignee: Microvascuar Therapeutics LLC, Tucson, AZ (US)

( * ) Notice: Subject to any disclaimer, the term of this patent is extended or adjusted under 35 U.S.C. 154(b) by 0 days.

(21) Appl. No.: 14/738,702

(22) Filed: Jun. 12, 2015

(65) Prior Publication Data

US 2016/0000943 A1    Jan. 7, 2016

Related U.S. Application Data

(60) Provisional application No. 62/011,469, filed on Jun. 12, 2014.

(51) Int. Cl.
*A61K 49/22* (2006.01)
(52) U.S. Cl.
CPC .................................. *A61K 49/223* (2013.01)

(58) Field of Classification Search
None
See application file for complete search history.

(56) References Cited

U.S. PATENT DOCUMENTS

| 6,572,840 | B1 | 6/2003 | Toler |
| 2004/0057906 | A1 | 3/2004 | Hsu et al. |
| 2005/0025710 | A1* | 2/2005 | Schneider ............ A61K 49/225 424/9.52 |
| 2013/0022550 | A1 | 1/2013 | Unger et al. |
| 2014/0134234 | A1 | 5/2014 | Grayburn et al. |

FOREIGN PATENT DOCUMENTS

WO    2010133700 A1    11/2010

OTHER PUBLICATIONS

International Search Report and Written Opinion dated Aug. 26, 2015 for International Application No. PCT/US2015/035681.

* cited by examiner

*Primary Examiner* — Michael G Hartley
*Assistant Examiner* — Jennifer Lamberski
(74) *Attorney, Agent, or Firm* — Milstein Zhang & Wu LLC

(57) ABSTRACT

A composition for stabilizing a fluorocarbon emulsion. That composition includes phosphatidylcholine, phosphatidylethanolamine-PEG, and a cone-shaped lipid.

12 Claims, 17 Drawing Sheets

PHOSPHOLIPID COMPOSITION AND MICROBUBBLES AND EMULSIONS FORMED USING SAME

CROSS REFERENCE TO RELATED APPLICATIONS

This Application claims priority to a United States Provisional Application filed Jun. 12, 2014 and having Ser. No. 62/011,469, wherein that Provisional Application is hereby incorporated herein by reference.

FIELD OF THE INVENTION

A phospholipid composition is disclosed. In certain embodiments, the phospholipid composition can be used as an ultrasound contrast agent ("USCA"), where that USCA comprises improved shelf-life and patient tolerability.

BACKGROUND OF THE INVENTION

Ultrasound contrast agents (USCA) are used for improving diagnostic accuracy on ultrasound imaging. USCA have also been used as cavitation nuclei for therapeutic procedures such as sonothrombolysis useful for treating stroke and heart attack. At the current time, however, the main use of USCA is for diagnosis.

A prior art ultrasound contrast agent is sold in commerce under the trademark DEFINITY. DEFINITY is a phospholipid-based ultrasound contrast agent comprising dipalmitoylphosphatidylcholine ("DPPC"), dipalmitoylphosphatidylethanolamine-PEG(5,000) ("DPPE-PEG5,000"), and dipalmitoylphosphatidic acid ("DPPA").

DEFINITY has a shelf-life of two-years at 4-8° C. Hydrolysis of the lipids is primarily responsible for degradation of the product. Clinical use of DEFINITY is known to cause back pain as a side-effect. The prescribing information for DEFINITY expressly discloses that back pain occurs in about 1.2% of patients. When such back pain does occur, that side effect can be very unpleasant for the patient and last up to 30 minutes or one hour.

SUMMARY OF THE INVENTION

Applicants' composition comprises a plurality of lipids that is substantially charge neutral at neutral pH, i.e. pH=7.0 useful for stabilizing emulsion and microbubbles of fluorocarbons. The formulation comprises phosphatidylcholine with a PEG'ylated lipid and a third lipid which is a cone-shaped lipid. In certain embodiments, the cone-shaped lipid is phosphatidylethanolamine. The formulation can generate emulsions and microbubbles that show enhanced stability to storage and show propensity to lessened side-effects. In certain embodiments, Applicants' composition may also include a fourth lipid which is a bifunctional PEG'ylated lipid. Because microbubbles and emulsion nanoparticles prepared with Applicants' composition are overall charge-neutral, those microbubbles/that emulsion comprises enhanced properties for targeting biologically relevant epitopes and biomarkers.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF PREFERRED EMBODIMENTS

Figure 1:
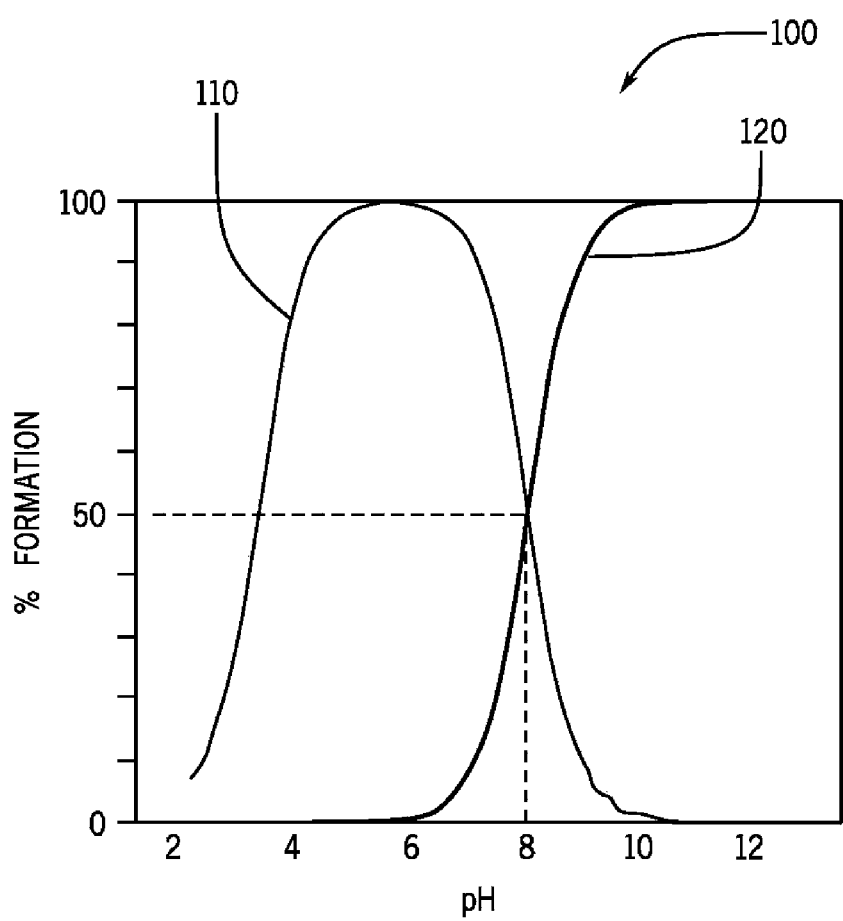
FIG. 1 shows the ionization of dipalmitoylphosphatidic acid at varying pH.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In certain embodiments, Applicant's phospholipid composition comprises one or more substantially charge-neutral phospholipids, wherein lipid coated microbubble-forming emulsions comprising Applicant's phospholipid composition comprise improved stability on storage, and lipid coated microbubbles formed from Applicant's microbubble-forming emulsions when used clinically are associated with a decrease in bioeffects, e.g. back pain. In certain embodiments, one or more of Applicants' phospholipids comprises a zwitterionic compound which is overall charge-neutral.

In certain embodiments, Applicant's phospholipid composition comprises dipalmitoylphosphatidylcholine ("DPPC"), phospholipid 1. DPPC is a zwitterionic compound, and is a substantially neutral phospholipid.

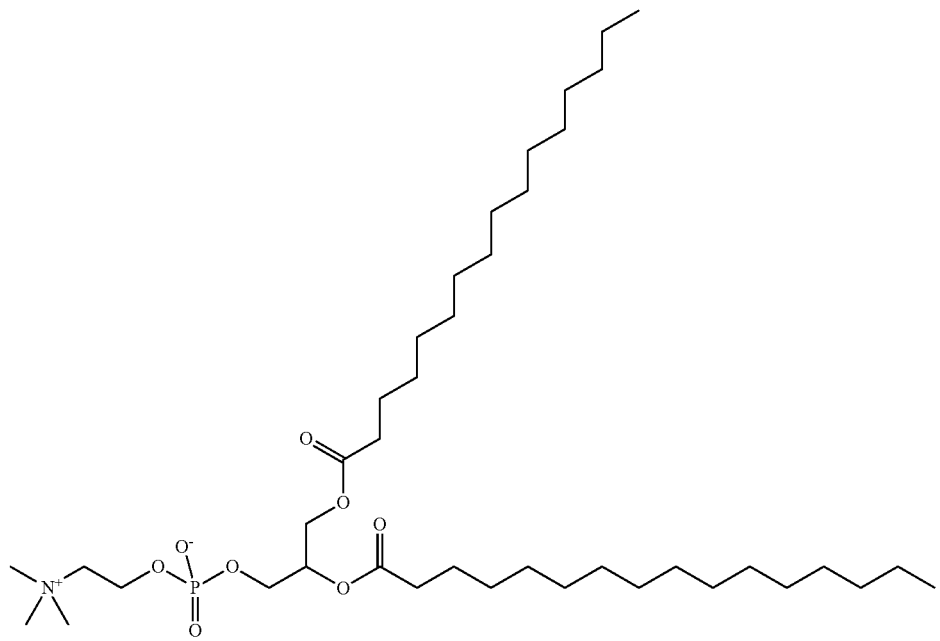

In certain embodiments, Applicants' phospholipid composition comprises a second phospholipid 2 comprising a polyhydroxy head group, and/or a headgroup of greater than 350 Daltons, wherein M is selected from the group consisting of Na$^+$, K$^+$, Li$^+$, and NH$_4^+$.

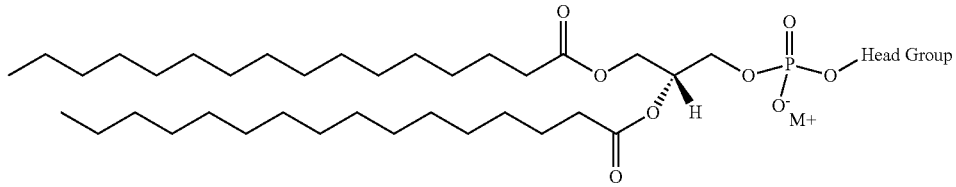

In certain embodiments, Applicant's phospholipid 2 comprises phospholipid 3 comprising a sodium cation and a glycerol headgroup bound to the phosphoryl moiety.

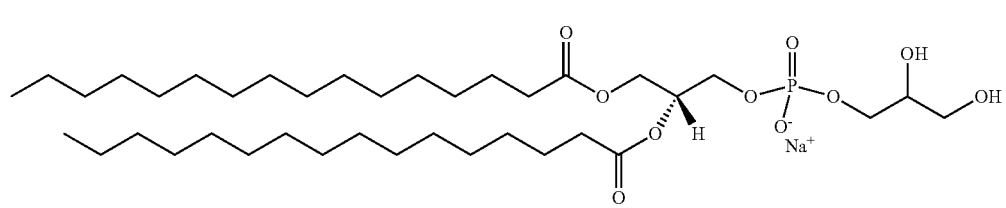

3

Phospholipid 4 comprises an ammonium counterion and a polyethylene glycol ("PEG") headgroup bound to the phosphoryl moiety. In certain embodiments, Applicants' composition comprises a PEG'ylated lipid. In certain embodiments, the PEG group MW is from about 1,000 to about 10,000 Daltons. In certain embodiments, the PEG group MW is from about 2,000 to about 5,000 Daltons. In certain embodiments, the PEG group MW is about 5,000 Daltons.

In certain embodiments, Applicants' lipid composition includes one or more of the following PEG'ylated lipids:
1,2-dimyristoyl-sn-glycero-3-phosphoethanolamine-N-[methoxy(polyethylene glycol)-1000] (ammonium salt),
1,2-dipalmitoyl-sn-glycero-3-phosphoethanolamine-N-[methoxy(polyethylene glycol)-1000] (ammonium salt),
1,2-distearoyl-sn-glycero-3-phosphoethanolamine-N-[methoxy(polyethylene glycol)-1000] (ammonium salt),
1,2-dioleoyl-sn-glycero-3-phosphoethanolamine-N-[methoxy(polyethylene glycol)-1000] (ammonium salt),
1,2-dimyristoyl-sn-glycero-3-phosphoethanolamine-N-[methoxy(polyethylene glycol)-2000] (ammonium salt),
1,2-dipalmitoyl-sn-glycero-3-phosphoethanolamine-N-[methoxy(polyethylene glycol)-2000] (ammonium salt),
1,2-distearoyl-sn-glycero-3-phosphoethanolamine-N-[methoxy(polyethylene glycol)-2000] (ammonium salt),
1,2-dioleoyl-sn-glycero-3-phosphoethanolamine-N-[methoxy(polyethylene glycol)-2000] (ammonium salt),
1,2-dimyristoyl-sn-glycero-3-phosphoethanolamine-N-[methoxy(polyethylene glycol)-3000] (ammonium salt),
1,2-dipalmitoyl-sn-glycero-3-phosphoethanolamine-N-[methoxy(polyethylene glycol)-3000] (ammonium salt),
1,2-distearoyl-sn-glycero-3-phosphoethanolamine-N-[methoxy(polyethylene glycol)-3000] (ammonium salt),
1,2-dioleoyl-sn-glycero-3-phosphoethanolamine-N-[methoxy(polyethylene glycol)-3000] (ammonium salt),
1,2-dimyristoyl-sn-glycero-3-phosphoethanolamine-N-[methoxy(polyethylene glycol)-5000] (ammonium salt),
1,2-dipalmitoyl-sn-glycero-3-phosphoethanolamine-N-[methoxy(polyethylene glycol)-5000] (ammonium salt),
1,2-distearoyl-sn-glycero-3-phosphoethanolamine-N-[methoxy(polyethylene glycol)-5000] (ammonium salt) and
1,2-dioleoyl-sn-glycero-3-phosphoethanolamine-N-[methoxy(polyethylene glycol)-5000] (ammonium salt)

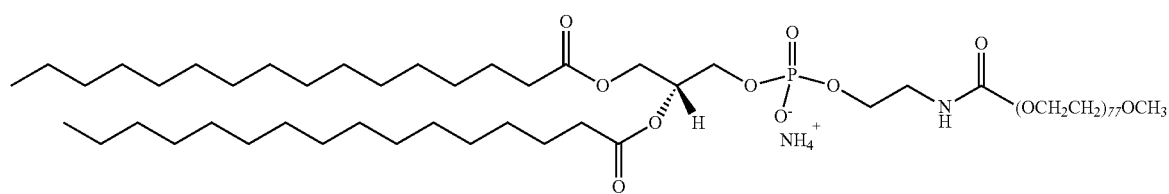

4

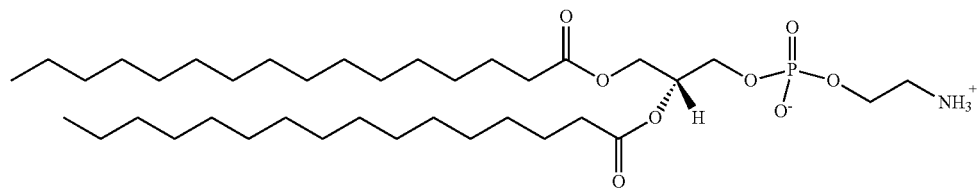

5

Phospholipid 5, shown above, represents dipalmitoylphosphatidylethanolamine, or DPPE. PE, particularly DPPE is a preferred lipid in the invention, preferably in the formulation with the other lipids at concentration of between 5 and 20 mole percent, most preferably 10 mole percent.

In certain embodiments, Applicant's phospholipid composition includes no Phosphatidic acid 6 ("DPPA").

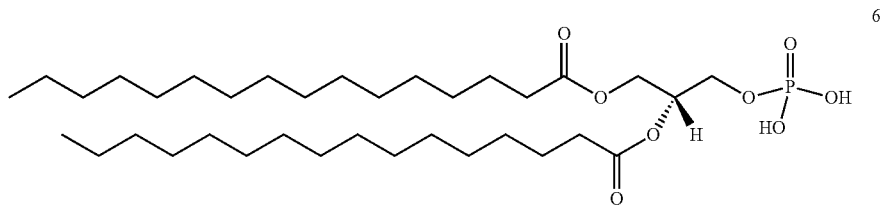 [SMILES: CCCCCCCCCCCCCCCC(=O)OC[C@H](COP(=O)(O)O)OC(=O)CCCCCCCCCCCCCCC]

As those skilled in the art will appreciate, DPPA comprises two acidic protons. The pKa for the second acidic proton is about 7.9. FIG. 1 graphically depicts the ionization of DPPA as a function of pH. Curve 110 recites the percent of mono-anion 6 present, and curve 120 recites the percent of di-anion 7 present. At a pH of about 4 and higher, the combined percentages of mono-anion 6 and di-anion 7 total 100.

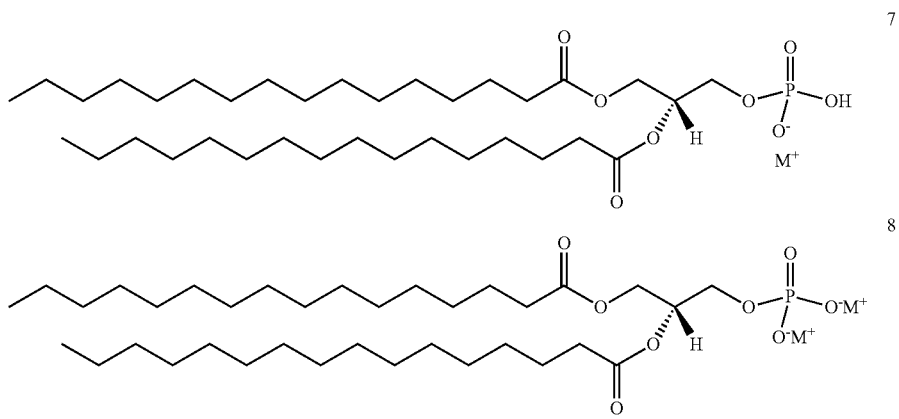

At a pH of about 7.9, DPPA comprises about 50 percent mono-anion 7 and about 50 percent di-anion 8. At a pH of about 7.0, DPPA comprises about 85 percent mono-anion 7 and about 15 percent di-anion 8.

Phosphatidic acid DPPA plays several roles in the functioning of cells; being utilized as a precursor in the biosynthesis of other lipids, facilitating vesicle fission/fusion via its biophysical properties and acting as a signaling lipid. The monoacyl derivative, lysophosphatidic acid (LPA), acts as a potent signaling molecule through the activation of high-affinity G-protein coupled receptors ($LPA_1$, $LPA_2$ and $LPA_3$, formerly, $EDG_2$, $EDG_4$ and $EDG_7$; and recently identified $LPA_4$, $LPA_5$ and $LPA_6$). As prior art phospholipid compositions comprising DPPA, such as for example DEFINITY, age and DPPA undergoes hydrolysis, the presence of the monoacyl derivative likely increases, with a clinical increase in undesirable bioeffects.

Table 1 shows the stability of a phospholipid composition comprising DPPA on storage at 4-8° C. The ratios of the individual lipid components are the ratios utilized in the prior art DEFINITY product. At 38 months of cold temperature storage DPPC is still 86.4% of its release level. DPPE-PEG 5,000 is 81.6% of its release level and DPPA is 78.4% of its release level.

At 48 months, however, the DPPA falls below its specification while DPPC and DPPE-PEG remained within specifications. Applicant has found that the phosphatidic acid DPPA is the limiting factor with respect to the cold storage stability of a phospholipid composition comprising a plurality of phospholipids in combination with DPPA. Furthermore, applicant has discovered that the other lipids are more stable in formulations without DPPA; it appears that DPPA catalyzes or accelerates the hydrolysis of the lipids in the formulation.

TABLE 1

|  |  | Time Points | | |
| --- | --- | --- | --- | --- |
| Test Parameter | Shelf-Life Specifications | Release | 14 Months | 38 Months |
| Appearance (n = 6) | Uniformly clear to translucent, colorless liquid | Pass | Pass | Pass |

TABLE 1-continued

| Test Parameter | | Shelf-Life Specifications | Release | 14 Months | 38 Months |
|---|---|---|---|---|---|
| Particulates (n = 6) | | Free of visible particles | Pass | Pass | Pass |
| pH (n = 2) | | 5.5-7.5 | 7.00 | 7.01 | 7.02 |
| Octafluoropropane Assay (mg/ml) (n = 5) | | ≥5.5 mg/ml | 7.60 | 6.91 | 6.619 |
| Lipid Assay (mg/ml) (n = 2) | DPPC | 0.864-1.296 | 1.116 | 1.090 | 0.964 |
| | DPPE-MPEG 5000 | 0.640-0.960 | 0.881 | 0.815 | 0.719 |
| | DPPA | 0.096-0.144 | 0.125 | 0.109 | 0.098 |
| Total Lipid (mg/ml) | | 1.60-2.40 | 2.12 | 2.01 | 1.781 |
| Size Distribution (particles/ml) (n = 6) | 0.56 µm to 1.06 µm | report only | 2.65E+10 | 1.95E+10 | 8.21E+09 |
| | 1.06 µm to 2.03 µm | ≥1.0 × 10$^8$ | 8.10E+09 | 6.96E+09 | 3.96E+09 |
| | 2.03 µm to 5.99 µm | ≥1.0 × 10$^7$ | 6.00E+08 | 4.38E+08 | 2.62E+08 |
| | 5.99 µm to 10.27 µm | report only | 6.96E+07 | 4.96E+07 | 1.75E+07 |
| | ≥10.27 µm | ≤5.0 × 10$^8$ | 4.40E+06 | 4.20E+06 | 2.85E+06 |
| | total | report only | 3.52E+10 | 2.69E+10 | 1.24E+10 |
| Endotoxin | | ≤80 EU/vial | Pass | NR | NR |
| Sterility | | Sterile | Pass | NR | Pass |

DPPA was incorporated into prior art phospholipids-based imaging agents to prevent possible aggregation of microbubbles. The di-anionic structure of DPPA resulted in increase electrostatic repulsion of lipid-coated microbubbles, thereby, it was thought reducing the likelihood of microbubble aggregation.

Surprisingly, Applicant has discovered that lipid-coated microbubbles prepared from a plurality of phospholipids but without DPPA do not undergo the undesirable aggregation. Moreover, lipid-coated microbubbles prepared from one or more phospholipids but without DPPA have similar particle size as DEFINITY.

In certain embodiments, Applicant's phospholipid composition comprises an injectable suspension. A vial for Applicant's injectable composition, upon activation, yields a plurality of phospholipid coated microspheres encapsulating a fluorocarbon gas. Such phospholipid-coated microspheres comprise a diagnostic drug that is intended to be used for contrast enhancement during certain indicated echocardiographic procedures.

Applicant's phospholipid composition comprises a clear, colorless, sterile, non-pyrogenic, hypertonic liquid, which upon activation provides a homogeneous, opaque, milky white injectable suspension of phospholipid coated microspheres encapsulating a fluorocarbon gas. In certain embodiments, that suspension is administered by intravenous injection.

Figure 2:
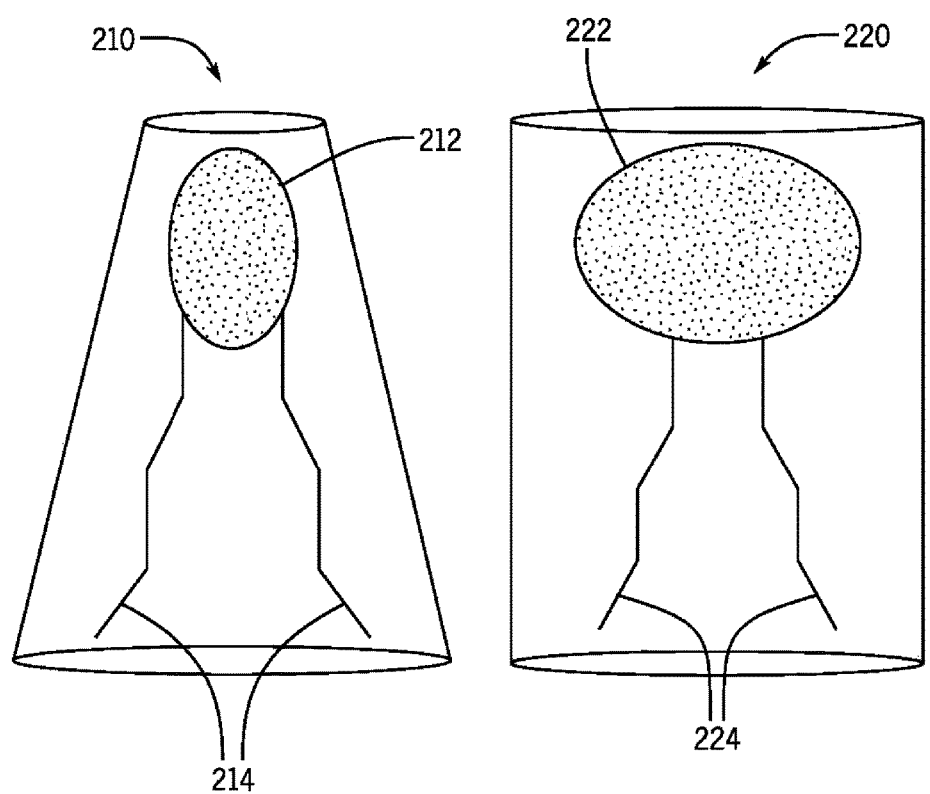
FIG. 2 illustrates a cone-shaped lipid and a cylindrical-shaped lipid.

Referring now to FIG. 2, in certain embodiments Applicants' invention contains one or more cone shaped or hexagonal HII forming lipids. Cone-shaped lipids, such as lipid 210, useful in the invention include monogalactosyldiacylglycerol (MGDG), monoglucosyldiacylglycerol (MGDG), diphosphatidylglycerol (DPG) also called cardiolipin, phosphatidylserine (PS), phosphatidylethanolamine (PE) and diacylglycerol. Phosphatidic acid (PA) is also a cone-shaped lipid, but is not preferred due to its propensity to hydrolysis and potential to cause bioeffects. The most preferred cone-shaped phospholipid is phoshatidylethanolamine (PE).

Cone shaped lipid 210 comprises a head group 212 that occupies a smaller volume than do the pendent groups 214 extending outwardly from head group 212. Cylindrical-shaped lipid 220 comprises a head group 222 that occupies a similar volume as that volume defined by the pendent groups 224 extending outwardly from head group 222. In addition the applicants have discovered that cationic, i.e. positively charged lipids can be used as cone shaped lipids provided that the head group of said cationic lipid is smaller than the tail.

Examples of potentially useful cone-shaped cationic lipids include but are not limited to 1,2-dioleoyl-3-trimethylammonium-propane (chloride salt), 1,2-dioleoyl-3-trimethylammonium-propane (methyl sulfate salt), 1,2-dimyristoyl-3-trimethylammonium-propane (chloride salt), 1,2-dipalmitoyl-3-trimethylammonium-propane (chloride salt), 1,2-distearoyl-3-trimethylammonium-propane (chloride salt), 1,2-dioleoyl-3-dimethylammonium-propane, 1,2-dimyristoyl-3-dimethylammonium-propane, 1,2-dipalmitoyl-3-dimethylammonium-propane, 1,2-distearoyl-3-dimethylammonium-propane, Dimethyldioctadecylammonium and 1,2-di-O-octadecenyl-3-trimethylammonium propane (chloride salt), O,O-di-O-octadecenyl-3-tα-trimethylammonioacetyl-diethanolamine.

Figure 3:
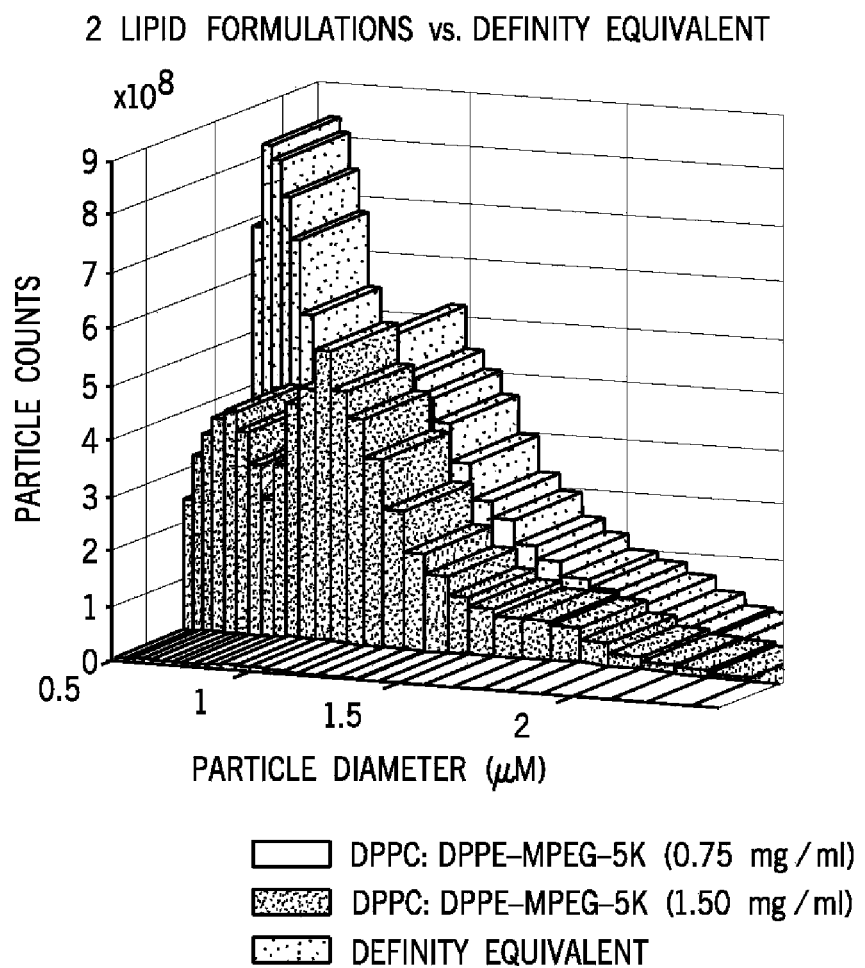
FIG. 3 graphically illustrates particle sizing for two (2) different formulations.

Referring now to FIG. 3, the inventors have discovered that microbubbles prepared with a third lipid—a cone-shaped lipid, in particular DPPE, provide better bubble count and better microbubble stability than formulations without such a third lipid. Preferably the cone-shaped lipid is provided within the formulation at a concentration of between about 5 and about 20 mole percent and more preferably at about 8 to 15 mole percent and most preferably at about 10% of the total lipid in the formulation.

As shown in FIG. 3, formulations without DPPA, and without a cone-shaped lipid. For example, the formulation comprising a lipid composition at 0.75 mg/ml generates few microbubbles. The formulation comprising a lipid composition at 1.50 mg/ml failed to generate microbubble particle counts similar to the Definity Equivalent.

In certain embodiments, Applicant's phospholipid composition comprises octafluoropropane encapsulated in an outer lipid shell consisting of (R)-4-hydroxy-N,N,N-trimethyl10-oxo-7-[(1-oxohexadecyl)oxy]-3,4,9-trioxa-4-phosphapentacosan-1-aminium, 4-oxide, inner salt, i.e. DPPC, and (R)-α-[6-hydroxy-6-oxido-9-[(1-oxohexadecyl)oxy]5,7,11-trioxa-2-aza-6-phosphahexacos-1-yl]-ω-methoxypoly(ox-1,2-ethanediyl), monosodium salt, i.e. DPPE PEG5000/

Phospholipid 4 with lipid 5, DPPE. DPPE-PEG5000 has an approximate molecular weight of 5750 Daltons.

Each mL of the clear liquid contains 0.75 mg lipid blend (consisting of consisting of 0.046 mg DPPE, 0.400 mg DPPC, and 0.304 mg MPEG5000 DPPE), 103.5 mg propylene glycol, 126.2 mg glycerin, 2.34 mg sodium phosphate monobasic monohydrate, 2.16 mg sodium phosphate dibasic heptahydrate, and 4.87 mg sodium chloride in Water for Injection. The pH is between 6.2-6.8.

After activation, each mL of Applicant's phospholipid coated microspheres encapsulating a fluorocarbon gas comprise a milky white suspension consisting essentially of a maximum of $1.2 \times 10^{10}$ lipid-coated microspheres, and about 150 microL/mL (1.1 mg/mL) octafluoropropane. The microsphere particle size parameters are listed below, and are identical to those of DEFINITY:

| | |
|---|---|
| Mean Particle Size | 1.1-3.3 μm |
| Particles Less than 10 μm | 98% |
| Maximum Diameter | 20 μm |

A comparison of the quantitative composition of Applicant's phospholipid composition and the prior art DEFINITY products is shown in TABLE 2, below.

In certain embodiments, Applicant's phospholipid composition is identical to DEFINITY, with the exception that Applicant's phospholipid composition does not include any DPPA, but that an equimolar amount of DPPE has been substituted for DPPA. Other components of the lipid blend (DPPC, DPPE PEG5000 and DPPe) have been proportionately increased to maintain the total lipid blend at 0.75 mg.

TABLE 2

| APPLICANT'S COMPOSITION | DEFINITY |
|---|---|
| Octafluoropropane | Octafluoropropane |
| Pre activation: in vial headspace | Pre activation: in vial headspace |
| Post activation: 1.1 mg/mL in lipid microspheres | Post activation: 1.1 mg/mL in lipid microspheres |
| 0.75 mg lipid blend (consisting of 0.046 mg DPPE, 0.400 mg DPPC, and 0.304 mg MPEG5000 DPPE) | 0.75 mg lipid blend (consisting of 0.045 mg DPP A, 0.401 mg DPPC, and 0.304 mg MPEG5000 DPPE) |
| 103.5 mg propylene glycol | 103.5 mg propylene glycol |
| 126.2 mg glycerin | 126.2 mg glycerin |
| 2.34 mg sodium phosphate monobasic monohydrate | 2.34 mg sodium phosphate monobasic monohydrate |
| 2.16 mg sodium phosphate dibasic heptahydrate | 2.16 mg sodium phosphate dibasic heptahydrate |
| 4.87 mg sodium chloride | 4.87 mg sodium chloride |
| Adjust pH to 6.2-6.8 with NaOH or HCl | Adjust pH to 6.2-6.8 with NaOH or HCl |
| Qs to 1 mL | Qs to 1 mL |

For the fourth lipid, a bifunctional PEG'ylated lipid may be employed. Bifunctional PEG'ylated lipids include but are not limited to DSPE-PEG(2000) Succinyl 1,2-distearoyl-sn-glycero-3-phosphoethanolamine-N-[succinyl(polyethylene glycol)-2000] (ammonium salt), DSPE-PEG(2000) PDP 1,2-distearoly-sn-glycero-3-phosphoethanolamine-N-[PDP (polyethylene glycol)-2000] (ammonium salt), DSPE-PEG (2000) Maleimide 1,2-distearoly-sn-glycero-3-phosphoethanolamine-N-[maleimide(polyethylene glycol)-2000] (ammonium salt), DSPE-PEG(2000) Biotin 1,2-distearoyl-sn-glycero-3-phosphoethanolamine-N-[maleimide(polyethylene glycol)-2000] (ammonium salt), DSPE-PEG(2000) Cyanur 1,2-distearoly-sn-glycero-3-phosphoethanolamine-N-[cyanur(polyethylene glycol)-2000] (ammonium salt), DSPE-PEG(2000) Amine 1,2-distearoyl;-sn-glycero-3-phosphoethanolamine-N-[amino(polyethylene glycol)-2000] (ammonium salt), DPPE-PEG(5,000)-maleimide, 1,2-distearoyl-sn-glycero-3-phosphoethanolamine-N-[dibenzocyclooctyl(polyethylene glycol)-2000] (ammonium salt), 1,2-distearoyl-sn-glycero-3-phosphoethanolamine-N-[azido(polyethylene glycol)-2000] (ammonium salt), 1,2-distearoyl-sn-glycero-3-phosphoethanolamine-N-[succinyl (polyethylene glycol)-2000] (ammonium salt), 1,2-distearoyl-sn-glycero-3-phosphoethanolamine-N-[carboxy (polyethylene glycol)-2000] (ammonium salt), 1,2-distearoyl-sn-glycero-3-phosphoethanolamine-N-[maleimide(polyethylene glycol)-2000] (ammonium salt), 1,2-distearoyl-sn-glycero-3-phosphoethanolamine-N-[PDP (polyethylene glycol)-2000] (ammonium salt), 1,2-distearoyl-sn-glycero-3-phosphoethanolamine-N-[amino(polyethylene glycol)-2000] (ammonium salt), 1,2-distearoyl-sn-glycero-3-phosphoethanolamine-N-[biotinyl(polyethylene glycol)-2000] (ammonium salt), 1,2-distearoyl-sn-glycero-3-phosphoethanolamine-N-[cyanur(polyethylene glycol)-2000] (ammonium salt), 1,2-distearoyl-sn-glycero-3-phosphoethanolamine-N-[folate(polyethylene glycol)-2000] (ammonium salt), 1,2-distearoyl-sn-glycero-3-phosphoethanolamine-N-[folate(polyethylene glycol)-5000] (ammonium salt), N-palmitoyl-sphingosine-1-{succinyl[methoxy(polyethylene glycol)2000]} and N-palmitoyl-sphingosine-1-{succinyl[methoxy(polyethylene glycol)5000]}.

The bifunctional lipids may be used for attaching antibodies, peptides, vitamins, glycopeptides and other targeting ligands to the microbubbles. The PEG chains MW may vary from about 1,000 to about 5,000 Daltons in the third lipid. In certain embodiments, the PEG chains MW are from about 2,000 to about 5,000 Daltons.

The lipid chains of the lipids used in the invention may vary from about 14 to about 20 carbons in length. Most preferably the chain lengths are from about 16 to about 18 carbons. Chains may be saturated or unsaturated but are preferably saturated. Cholesterol and cholesterol derivatives may also be employed in the invention with the proviso that they be neutral, or if negatively charged contain a head group greater than about 350 MW in juxtaposition to the negative charge to shield the charge from the biological milieu.

In various embodiments, the microbubble core gas is nitrogen, oxygen, sulfur hexafluoride, perfluoropropane, perfluorobutane, perfluoropentane, perfluorohexane or mixtures thereof. For the purposes of imaging and drug delivery, the ideal microbubble core gas has low aqueous solubility coupled with a boiling point below body temperature. This results in a microbubble with a long circulation time, a long useful life span, and high echogenic qualities.

Applicant's gaseous precursors include, for example, fluorinated carbons, perfluorocarbons, sulfur hexafluoride, perfluoro ethers and combinations thereof. As the stilled artisan will appreciate, a particular fluorinated compound, such as sulfur hexafluoride, a perfluorocarbon or a perfluoro ether, may exist in the liquid state when the compositions are first made, and are thus used as a gaseous precursor. Whether the fluorinated compound is a liquid generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As known to one skilled in the art, the effective boiling point of a substance may be related to the pressure to which that substance is exposed. This relationship is exemplified by the ideal gas law: PV=nRT, where P is pressure, V is volume, n is moles of substance, R is the gas constant, and T is temperature in ° K. The ideal gas law indicates that as pressure increases, the effective boiling point also increases. Conversely, as pressure decreases, the effective boiling point decreases.

Fluorocarbons for use as gaseous precursors in the compositions of the present invention include partially or fully fluorinated carbons, preferably perfluorocarbons that are saturated, unsaturated or cyclic. The preferred perfluorocarbons include, for example, perfluoromethane, perfluoroethane, perfluoropropane, perfluorocyclopropane, perfluorobutane, perfluorocyclobutane, perfluoropentane, perfluorocylcopentane, perfluorohexane, perfluorocyclohexane, and mixtures thereof. More preferably, the perfluorocarbon is perfluorohexane, perfluoropentane, perfluoropropane or perfluorobutane.

Preferred ethers include partially or fully fluorinated ethers, preferably perfluorinated ethers having a boiling point of from about 36° C. to about 60° C. Fluorinated ethers are ethers in which one or more hydrogen atoms is replaced by a fluorine atom. Preferred perfluorinated ethers for use as gaseous precursors in the present invention include, for example, perfluorotetrahydropyran, perfluoromethyltetrahydrofuran, perfluorobutylmethyl ether (e.g., perfluoro t-butylmethyl ether, perfluoro isobutyl methyl ether, perfluoro n-butyl methyl ether), perfluoropropylethyl ether (e.g., perfluoro isopropyl ethyl ether, perfluoro n-propyl ethyl other), perfluorocyclobutylmethyl ether, perfluorocyclopropylethyl ether, perfluoropropylmethyl ether (e.g., perfluoro isopropyl methyl ether, perfluoro n-propyl methyl ether), perfluorodiethyl ether, perfluorocyclopropylmethyl ether, perfluoromethylethyl ether and perfluorodimethyl ether.

Other preferred perfluoroether analogues contain between 4 and 6 carbon atoms, and optionally contain one halide ion, preferably Br—. For example, compounds having the structure Cn Fy Hx OBr, where n is an integer of from 1 to about 6, y is an integer of from 0 to about 13, and x is an integer of from 0 to about 13, are useful as gaseous precursors.

Other preferable fluorinated compounds for use as gaseous precursors in the present invention are sulfur hexafluoride and heptafluoropropane, including 1,1,1,2,3,3,3-heptafluoropropane and its isomer, 1,1,2,2,3,3,3-heptafluoropropane. Mixtures of different types of compounds, such as mixtures of a fluorinated compound (e.g., a perfluorocarbon or a perfluoroether) and another type of gas or gaseous precursor can also be used in the compositions of the present invention. Other gases and gaseous precursors are well known to one skilled in the art.

Generally, preferred gaseous precursors undergo phase transition to gas at a temperature up to about 57° C., preferably from about 20° C. to about 52° C., preferably from about 37° C., to about 50° C., more preferably from about 38° C. to about 48° C., even more preferably from about 38° C. to about 46° C., still even more preferably from about 38° C. to about 44° C., even still more preferably from about 38° C., to about 42° C. Most preferably, the gaseous precursors undergo a phase transition at a temperature of about less than 40° C. As will be recognized by one skilled in the art, the optimal phase transition temperature of a gaseous precursor for use in a particular application will depend upon considerations such as, for example, the particular patient, the tissue being targeted, the nature of the physiological stress state (i.e., disease, infection or inflammation, etc.) causing the increased temperature, the stabilizing material used, and/or the bioactive agent to be delivered.

Additionally, one skilled in the art will recognize that the phase transition temperature of a compound may be affected by local conditions within the tissue, such as, for example, local pressure (for example, interstitial, interfacial, or other pressures in the region). By way of example, if the pressure within the tissues is higher than ambient pressure, this will be expected to raise the phase transition temperature. The extent of such effects may be estimated using standard gas law predictions, such as Charles' Law and Boyle's Law. As an approximation, compounds having a liquid-to-gas phase transition temperature between about 30° C. and about 50° C. can be expected to exhibit about a 1° C. increase in the phase transition temperature for every 25 mm Hg increase in pressure. For example, the liquid-to-gas phase transition temperature (boiling point) of perfluoropentane is 29.5° C. at a standard pressure of about 760 mm Hg, but the boiling point is about 30.5° C. at an interstitial pressure of 795 mm Hg.

Materials used in stabilizing the gaseous precursor, discussed herein, may also affect the phase transition temperature of the gaseous precursor. In general, the stabilizing material is expected to increase the phase transition temperature of the gaseous precursor. In particular, a relatively rigid polymeric material, such as, for example, polycyanomethacrylate, may have a significant effect on the phase transition temperature of the gaseous precursor. Such an effect must be considered in the selection of the gaseous precursor and the stabilizing material.

The gaseous precursors and/or gases are preferably incorporated in the stabilizing materials and/or vesicles irrespective of the physical nature of the composition. Thus, it is contemplated that the gaseous precursors and/or gases may be incorporated, for example, in stabilizing materials in which the stabilizing materials are aggregated randomly, such as emulsions, dispersions or suspensions, as well as in vesicles, including vesicles which are formulated from lipids, such as micelles and liposomes. Incorporation of the gases and/or gaseous precursors in the stabilizing materials and/or vesicles may be achieved by using any of a number of methods.

The terms "stable" or "stabilized" mean that the vesicles may be substantially resistant to degradation, including, for example, loss of vesicle structure or encapsulated gas, gaseous precursor and/or bioactive agent, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

Useful gases in the invention are shown in Table 3 below.

TABLE 3

| Compound | Molecular Weight | Aqueous Solubility (Ostwald's Coefficient) | Boiling Point ° C. |
|---|---|---|---|
| Nitrogen | 28 | 18071 | −196 |
| Oxygen | 32 | 4865 | −183 |
| Sulfur Hexafluoride | 146 | 5950 | −64 |
| Perfluoropropane | 188 | 583 | −36.7 |
| Perfluorobutane | 238 | <500 | −1.7 |
| Perfluoropentane | 288 | >24 and <500 | 29 |
| Perfluorohexane | 338 | 24 | 56.6 |

The following examples are presented to further illustrate to persons skilled in the art how to make and use the invention. These examples are not intended as a limitation, however, upon the scope of the invention.

Example 1

A blend of lipids was prepared by suspending a mixture of lipids containing DPPC and DPPE-MPEG-5000 in propylene glycol. The lipid suspension was heated to 65±50 C until dissolution of the lipids in the propylene glycol was complete. The lipid solution was then added to an aqueous solution containing sodium chloride, phosphate buffer and glycerol and allowed to mix completely with gentle stirring. Each ml of the resultant lipid blend contained 0.75 mg total lipid (consisting of 0.43 mg DPPC, and 0.32 mg DPPE-MPEG-5000). Each ml of the lipid blend also contained 103.5 mg propylene glycol, 126.2 mg glycerin, 2.34 mg sodium phosphate monobasic monohydrate, 2.16 mg sodium phosphate dibasic heptahydrate, and 4.87 mg sodium chloride in Water for Injection. The pH was 6.2-6.8. The material was provided in sealed vials with a headspace containing octafluoropropane (OFP) gas (>80%) with the balance air.

Determination of the concentration and size distribution of the microbubbles produced by formulations listed in both previous and subsequent parts of this application were done in the following manner. Vials were activated using a Vialmix modified dental amalgamator and allowed to sit for 4 minutes before diluting a small amount of the microbubble suspension with filtered normal saline in a suitable container. After activation and dilution (1e-6) of the microbubble solution, microbubble size distributions were determined using a Nicomp 780 (Particle Sizing Systems) sampling in 128 channels. Microbubble particle sizing results obtained from lipid formulations listed in this application were compared with a Definity Equivalent standard. This standard contains approximately 82 mol % DPPC, 10 mol % DPPA, and 8 mol % DPPE-MPEG-5000 dissolved in the same buffered co-solvent saline mixture as the neutral formulation.

Example 2—Preparation of Different Formulations

As shown in Table 4, the mole percent ratios of DPPC:DPPE-MPEG-5K were adjusted from 91.16:8.84 to 94.00:6.00 at 0.75 mg/ml total with 92.55:7.45 being the most stable, as shown in Table 4. Stability was based on the opacity of the vials after activation.

TABLE 4

| FORM | DPPC | MPEG-5K-DPPE | TOTAL LIPID |
|---|---|---|---|
| 01 | 91.16 | 8.84 | 0.75 (mg/ml) |
| 02 | 92.00 | 8.00 | 0.75 (mg/ml) |
| 03 | 92.55 | 7.44 | 0.75 (mg/ml) |
| 04 | 94.00 | 6.00 | 0.75 (mg/ml) |

Additionally the volume percentages of propylene glycol and glycerol were also adjusted from 0 to 20% in the most stable of two lipid blends; this had no effect on microbubbles stability.

Figure 4:
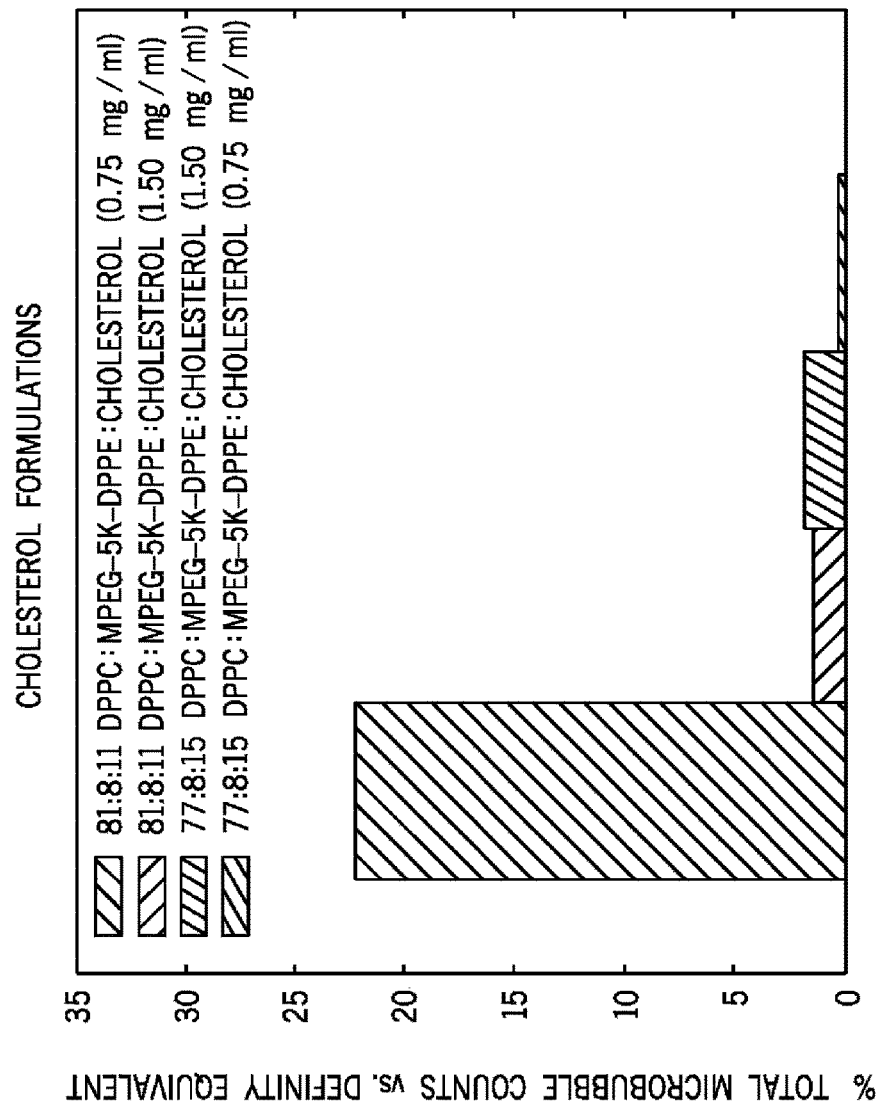
FIG. 4 graphically illustrates total microbubble counts for compositions containing cholesterol.

Lipid blends containing cholesterol are shown in Table 5 and Table 6. Lipid blend formulations containing cholesterol, DPPC and DPPE-MPEG-5000 at 0.75 and 1.50 mg/ml total lipid, produced lower concentrations of microbubbles than did the Definity standard formulation (FIG. 4). Of the four formulations containing cholesterol, the lipid blend with 81 mol % DPPC, 11 mol % DPPE-MPEG-5000, and 8% cholesterol produced the highest concentration of microbubbles.

Figure 5:
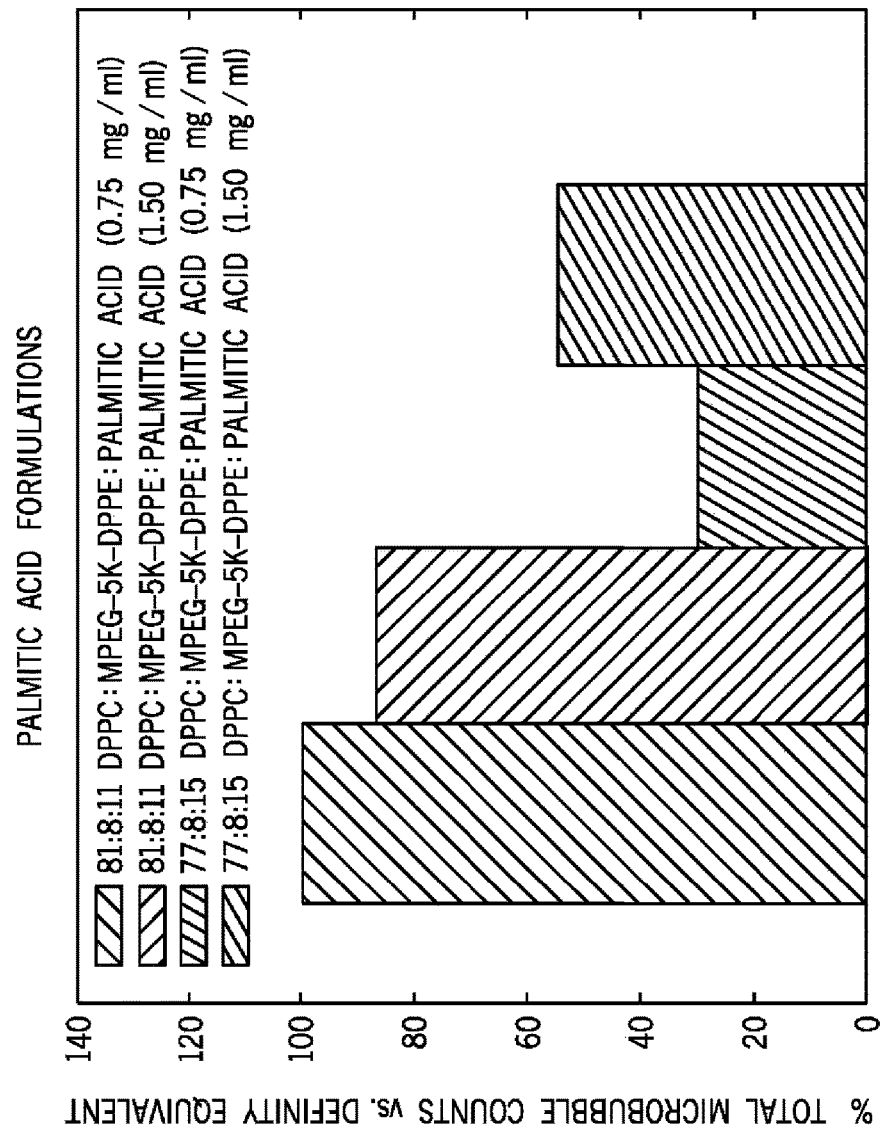
FIG. 5 graphically illustrates total microbubble counts for compositions containing palmitic acid.

Referring to FIG. 5, formulations containing palmitic acid, DPPC, and DPPE-MPEG-5000 consistently produced higher concentrations of microbubbles than did formulations containing only DPPC and DPPE-MPEG-5000. When compared against the Definity standard, these formulations produced a higher concentration of larger-sized bubbles that could pose a health risk. Other ingredients were added to the two lipid blend to optimize the concentration and size distribution of the microbubbles. These excipients included stearic acid, Pluronic F68, and 1,2-Distearoyl-sn-glycero-3-phosphoglycerol (DSPG). Formulations containing DSPG and stearic acid produced a higher concentration of microbubbles than formulations containing DPPC and DPPE-MPEG-5000, however not to the extent that formulations containing DPPE were able to (See Example 3). The addition of Pluronic F68 to the two lipid blend did not significantly increase the concentration of microbubbles.

TABLE 5

| | MOL % LIPID | | | | Microbubble Mean Size | |
|---|---|---|---|---|---|---|
| Form | DPPC | DPPE-MPEG-5K | Cholesterol | | Vol Wt | Num Wt |
| 13 | 80.93 | 7.88 | 10.55 | 0.75 mg/ml | 76.28 | 1.09 |
| 18 | 81.53 | 7.92 | 10.57 | 1.50 mg/ml | 77.93 | 1.58 |
| 20 | 77.22 | 7.45 | 15.32 | 1.50 mg/ml | 38.54 | 1.80 |
| 22 | 77.22 | 7.45 | 15.32 | 0.75 mg/ml | 435.67 | 1.87 |

TABLE 6

| | MOL % LIPID | | | | Microbubble Mean Size | |
|---|---|---|---|---|---|---|
| Form | DPPC | DPPE-MPEG-5K | Cholesterol | | Vol Wt | Num Wt |
| 17 | 80.93 | 7.88 | 11.19 | 0.75 mg/ml | 432.46 | 0.89 |
| 19 | 80.93 | 7.88 | 11.19 | 1.50 mg/ml | 23.04 | 0.89 |
| 21 | 73.16 | 6.61 | 20.23 | 0.75 mg/ml | 12.60 | 0.88 |
| 23 | 73.16 | 6.61 | 23.23 | 1.50 mg/ml | 389.41 | 0.93 |

Example 3

Preparation of MVT-100 (Formulation Containing DPPE)

A blend of lipids containing DPPC, DPPE and DPPE-MPEG-5000 was prepared using similar methods to those listed in Example 1. The lipids, suspended in propylene glycol, were heated to 70±50 C until they dissolved. The lipid solution was then added to an aqueous solution containing sodium chloride, phosphate buffer and glycerol and allowed to mix completely by stirring. Each ml of the resultant lipid blend contained 0.75 mg total lipid (consisting of 0.400 mg DPPC, 0.046 mg DPPE, and 0.32 mg MPEG-5000-DPPE). Each ml of the lipid blend also contained 103.5 mg propylene glycol, 126.2 mg glycerin, 2.34 mg sodium phosphate monobasic monohydrate, 2.16 mg sodium phosphate dibasic heptahydrate, and 4.87 mg sodium chloride in Water for Injection. The pH was 6.2-6.8. The material was provided in sealed vials with a headspace containing octafluoropropane (OFP) gas (>80%) with the balance air.

Figure 6:
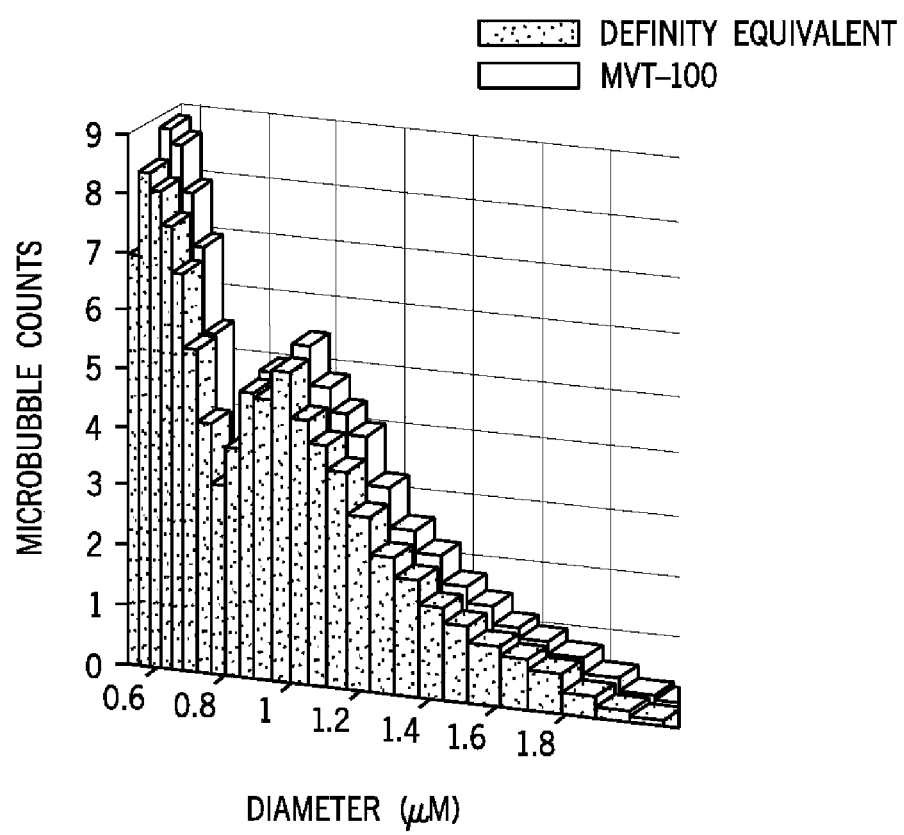
FIG. 6 graphically illustrates particle count versus particle diameter for MVT-100 and a DEFINITY EQUIVALENT.

FIG. 6 graphically illustrates the sizing profile of microbubbles produced by the Definity equivalent standard and MVT-100. Both formulations have identical lipid concentration and composition with the exception of substitution of DPPE in MVT-100 for DPPA. The microbubbles produced by the MVT-100 formulation remain stable over time with respect to concentration and size distribution even while suspended in normal saline. Referring now to FIGS. 7, 8, 9 and 10. Lipid blends containing different mixtures of the lipids DPPC, DPPE, and DPPE-MPEG-5000 were made with different proportions of the co-solvents propylene glycol (PGOH), glycerol (GLOH), and water containing a sodium phosphate buffer and sodium chloride ($H_2O$). The recited co-solvent percentage ratios are listed as volume percent abbreviated as % (v/v). For example 10:10:80, equates to 10% (v/v) propylene glycol, 10% (v/v) glycerol and 80% (v/v) water containing sodium phosphate buffer and sodium chloride. The lipid blends are listed below in table 7.

The lipid blend containing 82 mol % DPPC, 10 mol % DPPE, and 8% DPPE-MPEG-5000 was prepared with both a sodium phosphate buffer as well as a Histidine-Glutamic Acid buffer. The lipid blend was also prepared with a sodium phosphate buffer at approximate concentrations of 5 and 25 mM. Other buffers approved for use in parenteral formulations with a pKa in the 5.8-7.8 range such as citric acid may be used as well. Gas filling in the final product may be 35% air with 65% perfluoropropane. But in these experiments the vials that we filled using the manifold for introducing the perfluoropropane were >90% for all samples.

Figure 7:
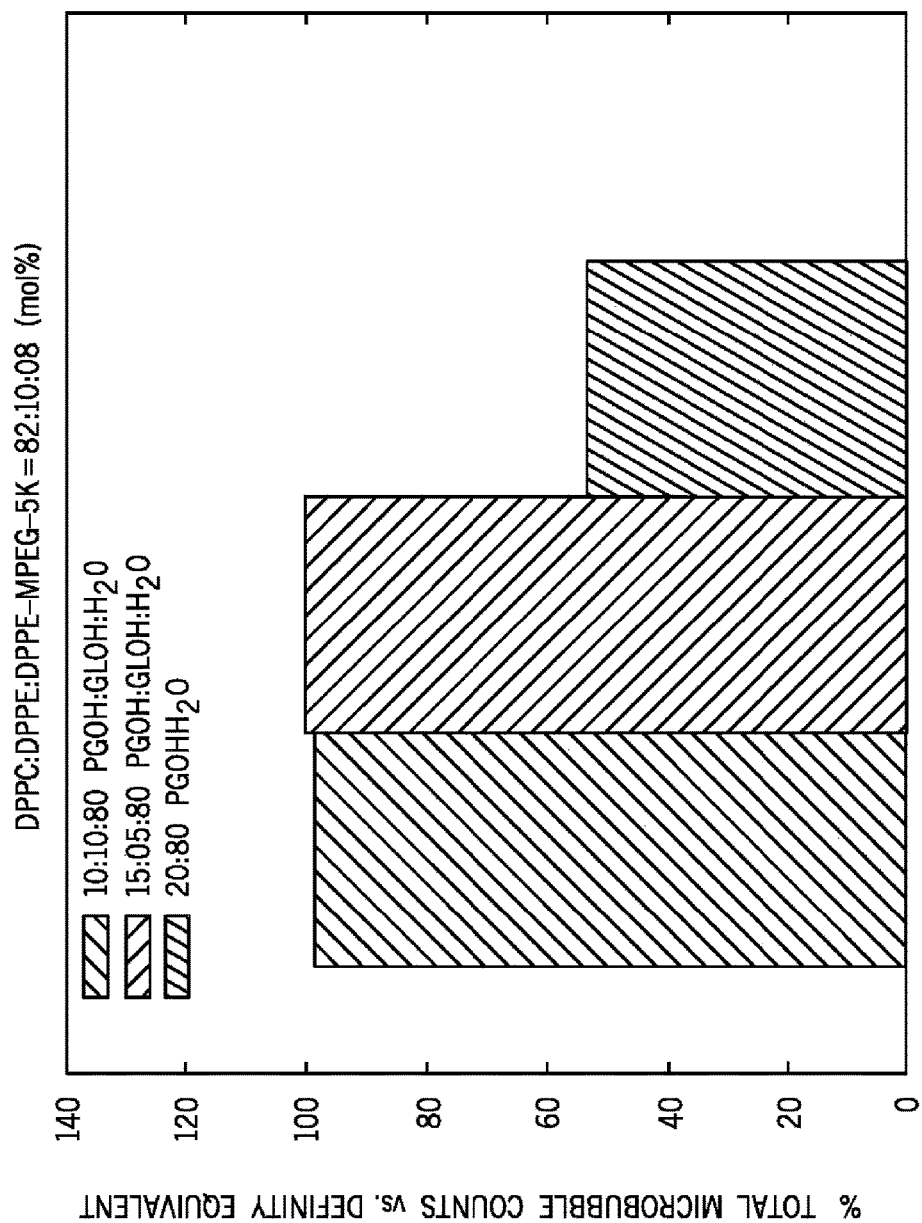
FIG. 7 graphically illustrates total microbubble counts versus DEFINITY EQUIVALENT for different ratios of diluents.

FIG. 7 is a comparison of formulations containing different concentrations of co-solvents with the same concentration of lipids (82 mol % DPPC, 10 mol % DPPE, 8 mol % DPPE-MPEG-5000). Formulations containing PGOH:GLOH:$H_2O$ at both 10:10:80 and 15:5:80% (v/v) produced similar microbubble concentrations as the Definity Equivalent standard which contains PGOH:GLOH:$H_2O$ at 10:10:80% (v/v). The formulation containing PGOH:$H_2O$ at 20:80% (v/v) produced a lower concentration of microbubbles than both the lipid blends containing 10:10:80 and 15:5:80 (v/v) PGOH:GLOH:$H_2O$ and the Definity Equivalent standard.

Figure 8:
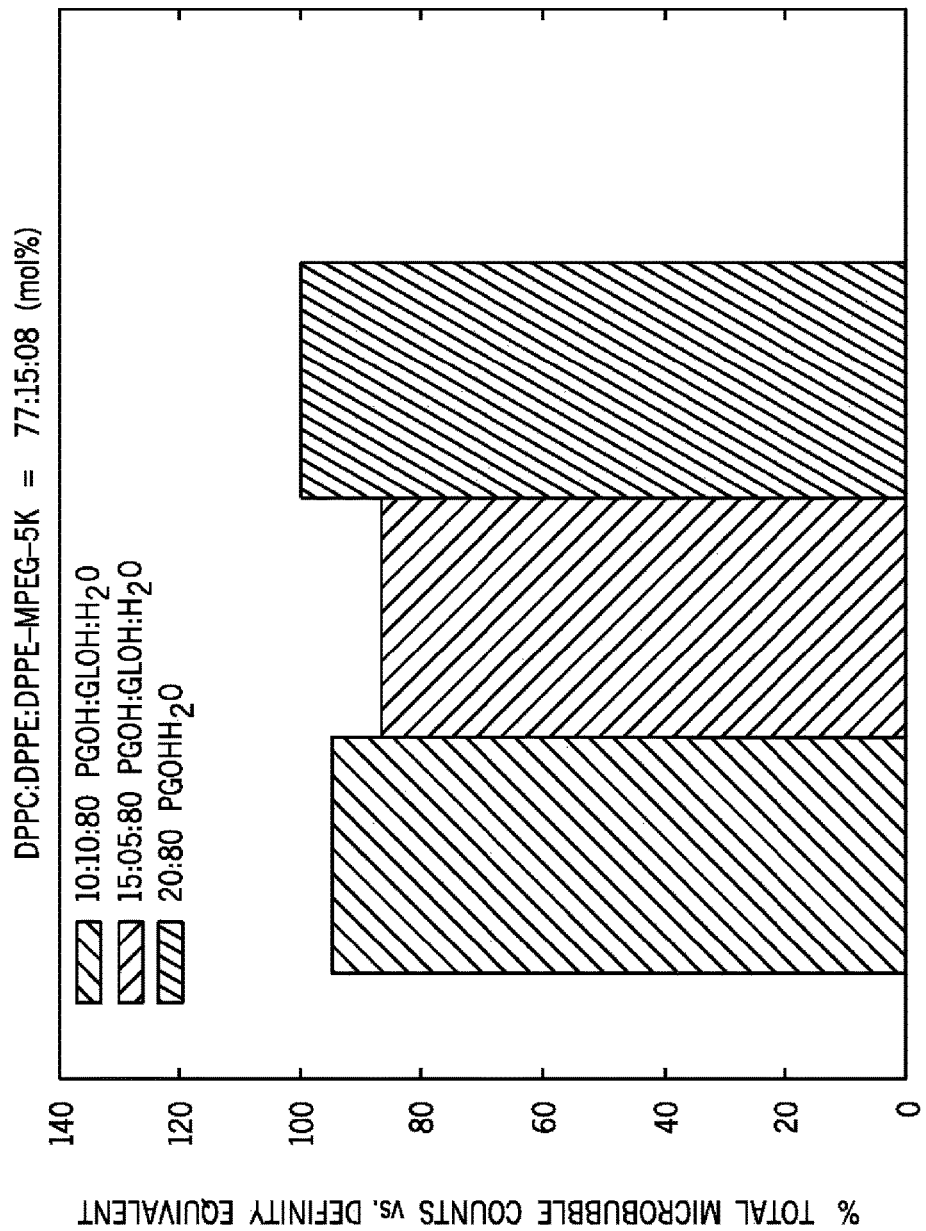
FIG. 8 graphically illustrates total microbubble counts versus DEFINITY EQUIVALENT for different ratios of diluents.

FIG. 8 is a comparison of formulations containing different concentrations of co-solvents with the same concentration of lipids (77 mol % DPPC, 15 mol % DPPE, 8 mol % DPPE-MPEG-5000). Changing the volume fraction of co-solvents did not significantly affect the concentration of microbubbles produced by the lipid blend.

Figure 9:
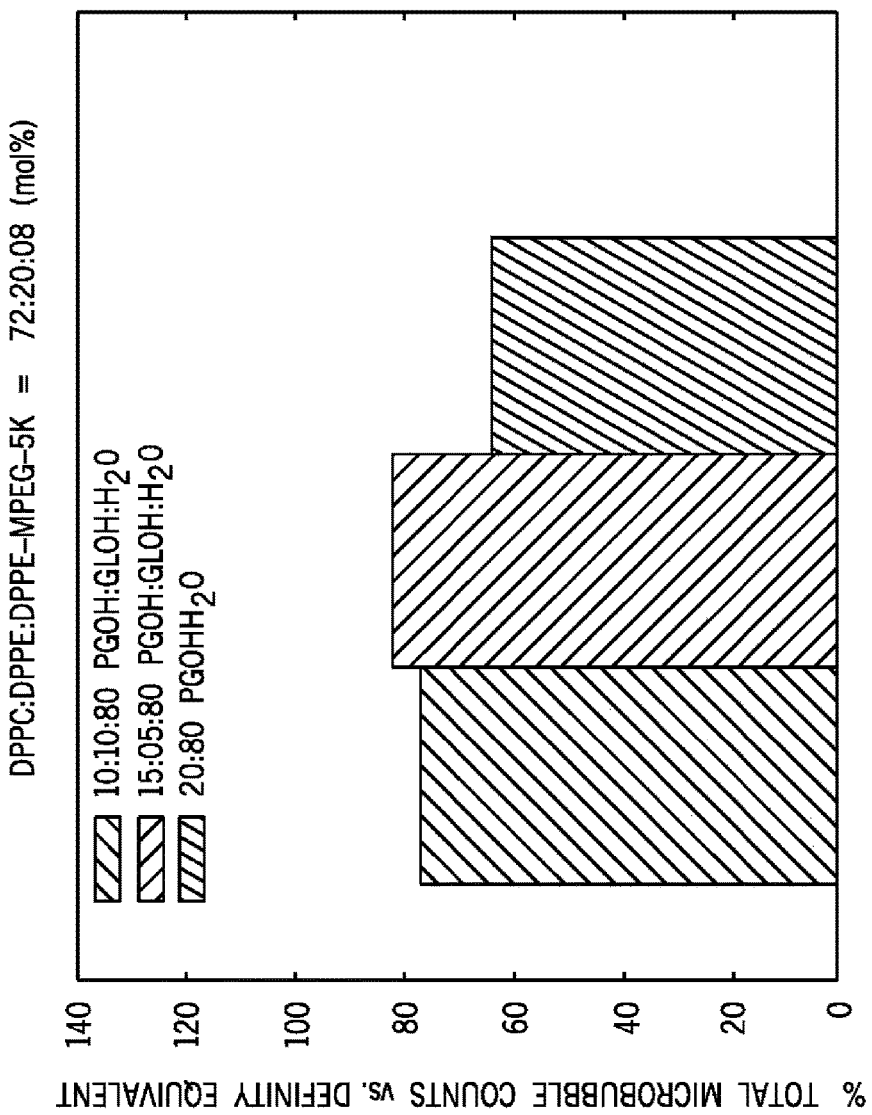
FIG. 9 graphically illustrates total microbubble counts versus DEFINITY EQUIVALENT for different ratios of diluents.

FIG. 9 is a comparison of formulations containing different concentrations of co-solvents with the same concentration of lipids (72 mol % DPPC, 20 mol % DPPE, 8 mol % DPPE-MPEG-5000). Increasing the percentage of DPPE to 20 mole % decreases the number of microbubbles compared to 10-15 mole % DPPE. Changing the volume fraction of co-solvents did not significantly affect the concentration of microbubbles produced by the lipid blend.

Figure 10:
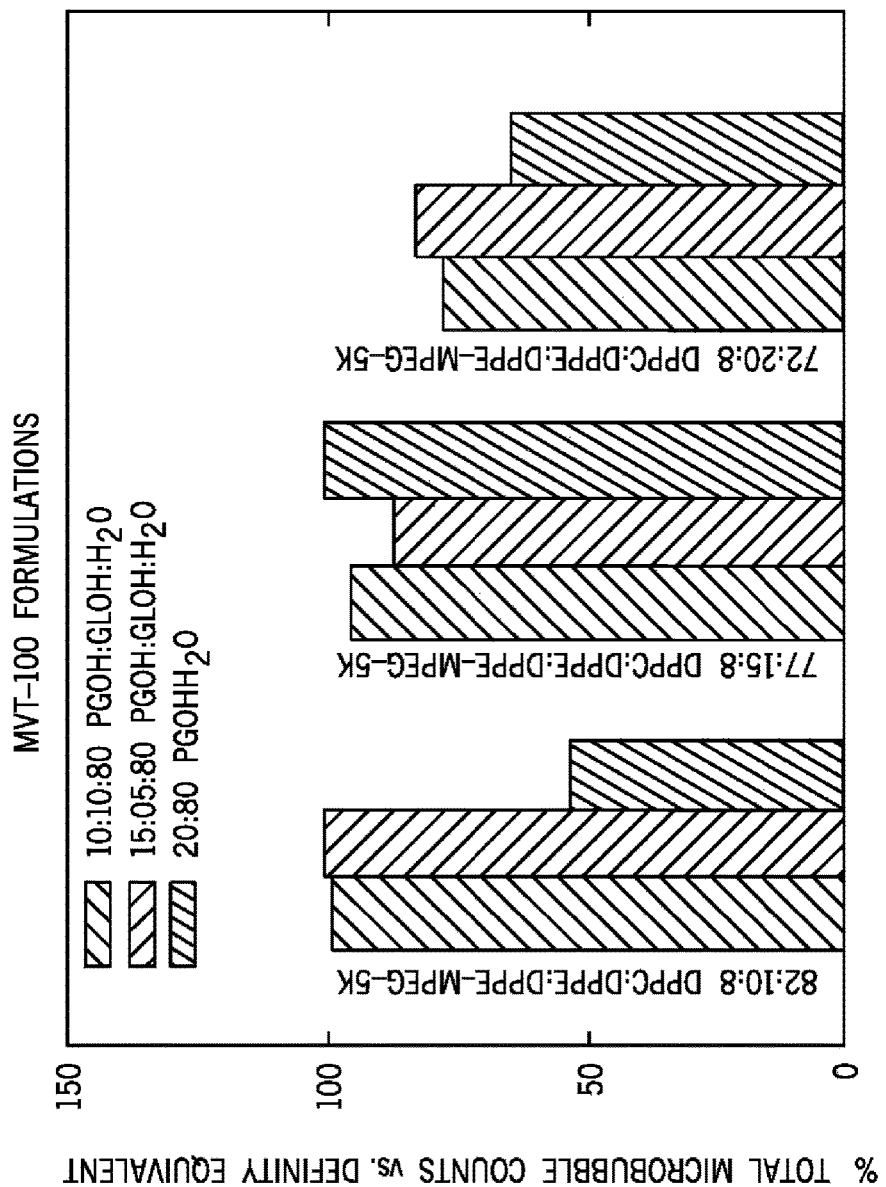
FIG. 10 graphically illustrates percent total microbubble counts versus DEFINITY EQUIVALENT for three different lipid ratios with different diluents.

FIG. 10 is a summary slide of the information shown in FIGS. 7, 8 and 9.

Example 4

Samples of Definity equivalent and MVT-100 lipid blends were prepared as described in Examples #1 and #3. HPLC was used to characterize the concentrations of DPPC, DPPE-MPEG-5000, DPPA, DPPE and palmitic acid (breakdown product of phospholipids from hydrolysis). Samples were stored at 4° C. and 40° C. and assayed after 31 days. Referring to Table 8 and Table 9, the degradation of the 3 lipids contained in the Definity equivalent (DPPA, DPPC, and DPPE-MPEG-5K) were significantly higher than the degradation of the 3 lipids contained in the MVT-100 formulation (DPPC, DPPE, DPPE-MPEG-5000). As shown in the bottom of Table 8, none of the lipids in the Definity equivalent retain over 90% potency after 31 days of storage at 40° C. and only one of the lipids is above 88% potency.

TABLE 7

| Mol % lipid ratios | Vol % cosolvent ratios | Total lipid conc | Vial fill volumes |
|---|---|---|---|
| 82:10:08 DPPC:DPPE:DPPE-MPEG-5K | 10:10:80 PGOH:GLOH:$H_2O$ | 0.75 mg/mL | 1.5 mL |
| 82:10:08 DPPC:DPPE:DPPE-MPEG-5K | 15:05:80 PGOH:GLOH:$H_2O$ | 0.75 mg/mL | 1.5 mL |
| 82:10:08 DPPC:DPPE:DPPE-MPEG-5K | 20:80 PGOH:$H_2O$ | 0.75 mg/mL | 1.5 mL |
| 77:15:08 DPPC:DPPE:DPPE-MPEG-5K | 10:10:80 PGOH:GLOH:$H_2O$ | 0.75 mg/mL | 1.5 mL |
| 77:15:08 DPPC:DPPE:DPPE-MPEG-5K | 15:05:80 PGOH:GLOH:$H_2O$ | 0.75 mg/mL | 1.5 mL |
| 77:15:08 DPPC:DPPE:DPPE-MPEG-5K | 20:80 PGOH:$H_2O$ | 0.75 mg/mL | 1.5 mL |
| 72:20:08 DPPC:DPPE:DPPE-MPEG-5K | 10:10:80 PGOH:GLOH:$H_2O$ | 0.75 mg/mL | 1.5 mL |
| 72:20:08 DPPC:DPPE:DPPE-MPEG-5K | 15:05:80 PGOH:GLOH:$H_2O$ | 0.75 mg/mL | 1.5 mL |
| 72:20:08 DPPC:DPPE:DPPE-MPEG-5K | 20:80 PGOH:$H_2O$ | 0.75 mg/mL | 1.5 mL |
| 82:10:08 DPPC:DPPE:DPPE-MPEG-5K | 10:10:80 PGOH:GLOH:$H_2O$ | 0.75 mg/mL | 1.0 mL |
| 82:10:08 DPPC:DPPE:DPPE-MPEG-5K | 15:05:80 PGOH:GLOH:$H_2O$ | 0.75 mg/mL | 1.0 mL |
| 82:10:08 DPPC:DPPE:DPPE-MPEG-5K | 10:10:80 PGOH:GLOH:$H_2O$ | 1.00 mg/mL | 1.5 mL |
| 82:10:08 DPPC:DPPE:DPPE-MPEG-5K | 10:10:80 PGOH:GLOH:$H_2O$ | 1.50 mg/mL | 1.5 mL |
| 77:15:08 DPPC:DPPE:DPPE-MPEG-5K | 10:10:80 PGOH:GLOH:$H_2O$ | 1.00 mg/mL | 1.0 mL |
| 77:15:08 DPPC:DPPE:DPPE-MPEG-5K | 10:10:80 PGOH:GLOH:$H_2O$ | 1.50 mg/mL | 1.0 mL |
| 77:15:08 DPPC:DPPE:DPPE-MPEG-5K | 15:05:80 PGOH:GLOH:$H_2O$ | 1.00 mg/mL | 1.0 mL |

Figure 11:
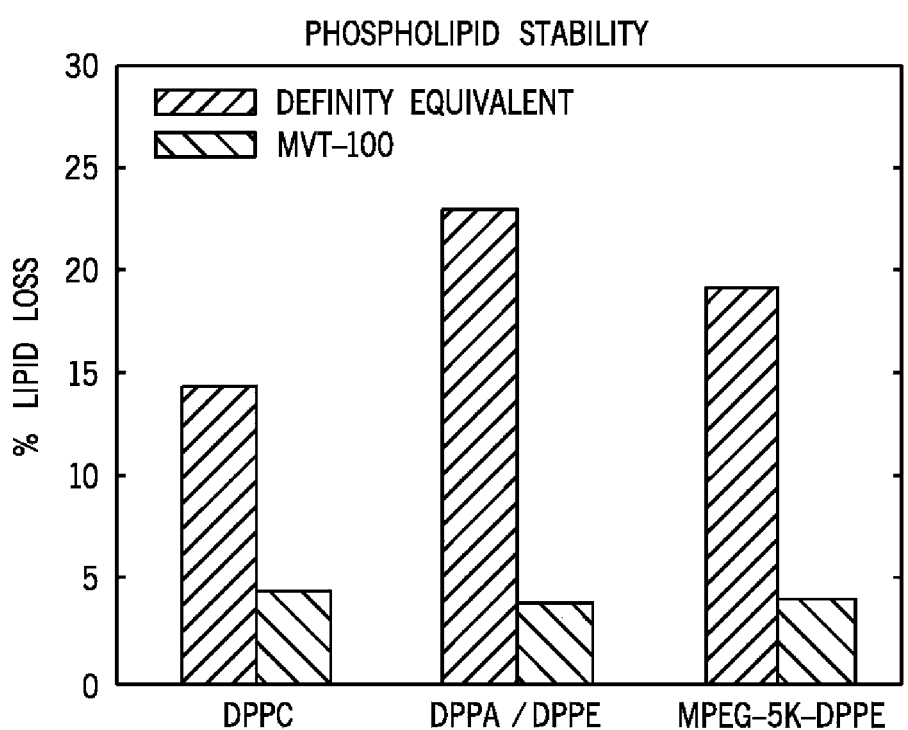
FIG. 11 graphically illustrates stability data for a DEFINITY EQUIVALENT comprising DPPA and for MVT-100 comprising DPPE instead of DPPA.

By comparison all of the lipids in MVT-100 retain >95% potency as shown in the bottom of Table 9. This difference in lipid degradation rates is illustrated in FIG. 11.

TABLE 8

Table 4. DEFINITY EQUIVALENT Stability

| | | Conc (mg/ml) | | | |
|---|---|---|---|---|---|
| | | Palm Acid | DPPE-MPEG-5K | DPPA | DPPC |
| BATCH 1 | T = 00 days | 0.000 | 0.282 | 0.046 | 0.379 |
| | | 0.000 | 0.283 | 0.047 | 0.380 |
| | | 0.000 | 0.284 | 0.047 | 0.384 |
| | T = 31 days | 0.035 | 0.242 | 0.038 | 0.311 |
| | | 0.035 | 0.251 | 0.039 | 0.319 |
| | | 0.035 | 0.251 | 0.038 | 0.319 |
| BATCH 2 | T = 00 days | 0.000 | 0.283 | 0.047 | 0.384 |
| | | 0.000 | 0.288 | 0.048 | 0.387 |
| | | 0.000 | 0.280 | 0.047 | 0.384 |
| | T = 31 days | 0.037 | 0.238 | 0.038 | 0.307 |
| | | 0.037 | 0.239 | 0.036 | 0.297 |
| | | 0.036 | 0.234 | 0.035 | 0.312 |
| BATCH 3 | T = 00 days | 0.000 | 0.306 | 0.045 | 0.420 |
| | | 0.000 | 0.307 | 0.045 | 0.429 |
| | | 0.000 | 0.311 | 0.044 | 0.428 |
| | T = 31 days | 0.031 | 0.266 | 0.031 | 0.344 |
| | | 0.031 | 0.265 | 0.034 | 0.341 |
| | | 0.033 | 0.265 | 0.032 | 0.343 |

| % Lipid (T = 31 days) | | | |
|---|---|---|---|
| BATCH | DPPE-MPEG-5K | DPPA | DPPC |
| 1 | 87.594 | 82.525 | 82.989 |
| 2 | 83.425 | 76.726 | 79.358 |
| 3 | 86.190 | 71.973 | 80.503 |
| Average | 85.736 | 77.075 | 80.95 |

TABLE 9

Table 5. MVT-100 Stability

| | | Conc (mg/ml) | | | |
|---|---|---|---|---|---|
| | | Palm Acid | DPPE-MPEG-5K | DPPA | DPPC |
| BATCH 1 | T = 00 days | 0.000 | 0.291 | 0.404 | 0.049 |
| | | 0.000 | 0.291 | 0.399 | 0.049 |
| | | 0.000 | 0.290 | 0.394 | 0.047 |
| | T = 31 days | 0.000 | 0.282 | 0.377 | 0.046 |
| | | 0.000 | 0.275 | 0.385 | 0.045 |
| | | 0.000 | 0.283 | 0.395 | 0.045 |
| BATCH 2 | T = 00 days | 0.000 | 0.294 | 0.409 | 0.044 |
| | | 0.000 | 0.288 | 0.397 | 0.045 |
| | | 0.000 | 0.281 | 0.398 | 0.044 |
| | T = 31 days | 0.000 | 0.274 | 0.386 | 0.043 |
| | | 0.000 | 0.273 | 0.380 | 0.043 |
| | | 0.000 | 0.273 | 0.386 | 0.043 |
| BATCH 3 | T = 00 days | 0.000 | 0.278 | 0.393 | 0.049 |
| | | 0.000 | 0.280 | 0.394 | 0.050 |
| | | 0.000 | 0.278 | 0.390 | 0.049 |

TABLE 9-continued

Table 5. MVT-100 Stability

| | | | | |
|---|---|---|---|---|
| T = 31 days | 0.000 | 0.269 | 0.377 | 0.048 |
| | 0.000 | 0.268 | 0.373 | 0.048 |
| | 0.000 | 0.264 | 0.376 | 0.049 |

| % Lipid (T = 31 days) | | | |
|---|---|---|---|
| BATCH | DPPE-MPEG-5K | DPPC | DPPE |
| 1 | 96.270 | 96.653 | 93.695 |
| 2 | 95.022 | 95.612 | 97.347 |
| 3 | 95.929 | 95.584 | 97.554 |
| Average | 95.740 | 95.950 | 96.199 |

Example 5

Figure 17:
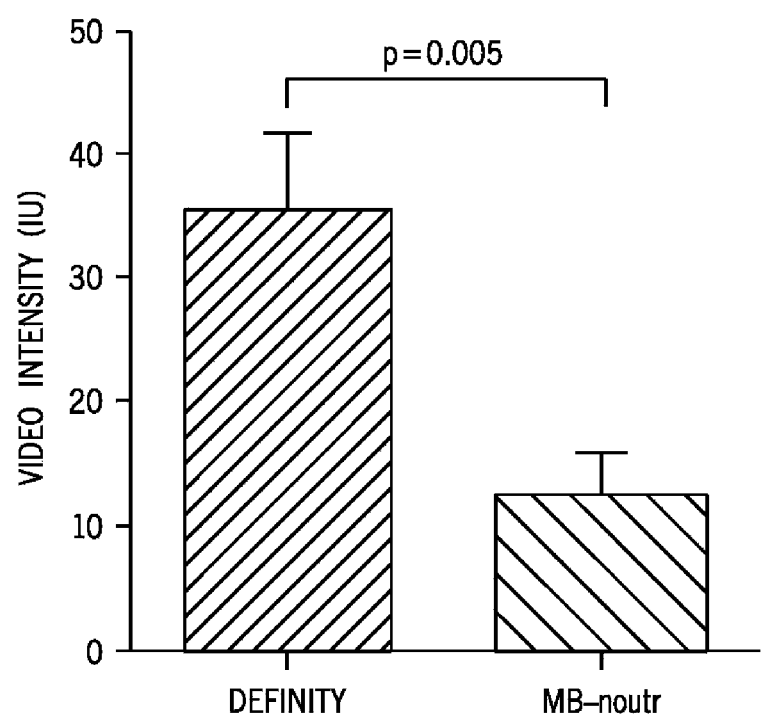
FIG. 17 graphically shows ultrasound imaging data relating to residual microbubbles in the renal cortices, where a Definity equivalent accumulated over three-fold more residual microbubbles in the renal cortices than did MVT-100.

Complement-mediated retention of microbubbles in the renal cortex is hypothesized to be responsible for back/flank pain that occurs as a side-effect of Definity. A study was performed with Definity equivalent and MVT-100 in wild-type mice. Mice were injected IV with either Definity equivalent (n=10) or MVT-100 (n=10) at a dose of $5 \times 10^5$ microbubbles. Ultrasound imaging was performed 8 minutes after microbubbles injection, allowing enough time for blood pool microbubbles to clear. Referring now to FIG. 17, residual microbubbles in the renal cortices were detected on ultrasound. Definity equivalent accumulated over three-fold more in the renal cortices than MVT-100. The data graphically shown in FIG. 17 demonstrate that MVT-100 has less renal retention than Definity equivalent, and suggest that MVT-100 should have a lower incidence of back/flank pain than Definity.

Figure 12:
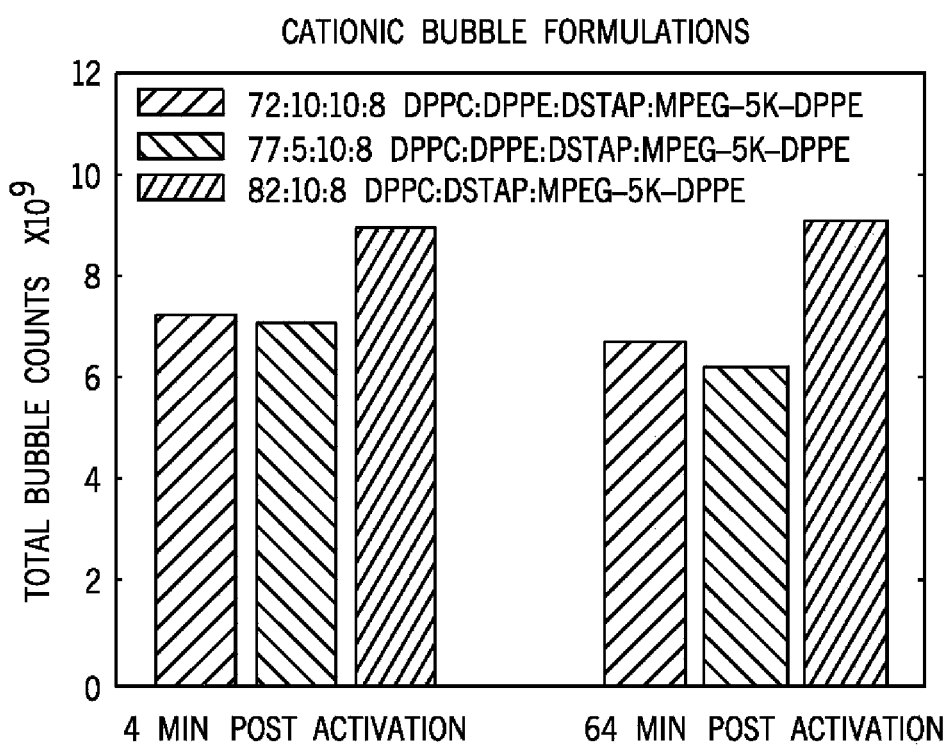
FIG. 12 graphically illustrates total microbubble counts measured for two different formulations wherein each formulation includes a cationic lipid in combination with a cone-shaped lipid and a third formulation where the cationic lipid replaces DPPE as the cone-shaped lipid.
Figure 13:
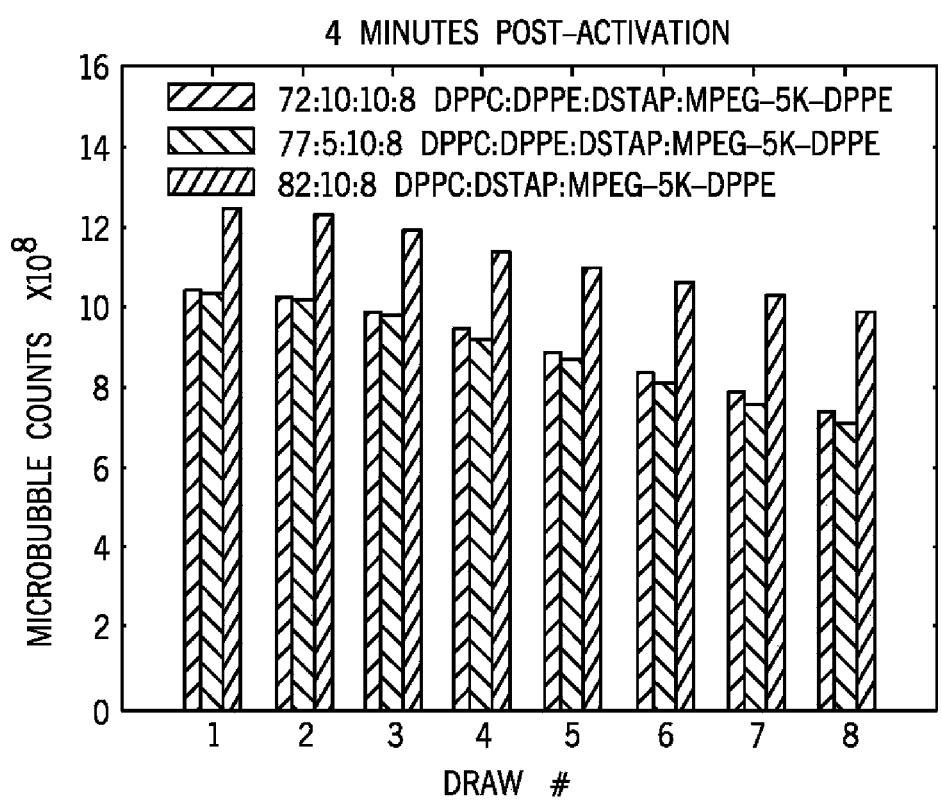
FIG. 13 graphically illustrates microbubble counts for each of the formulations recited versus Draw# at four (4) minutes post activation.
Figure 14:
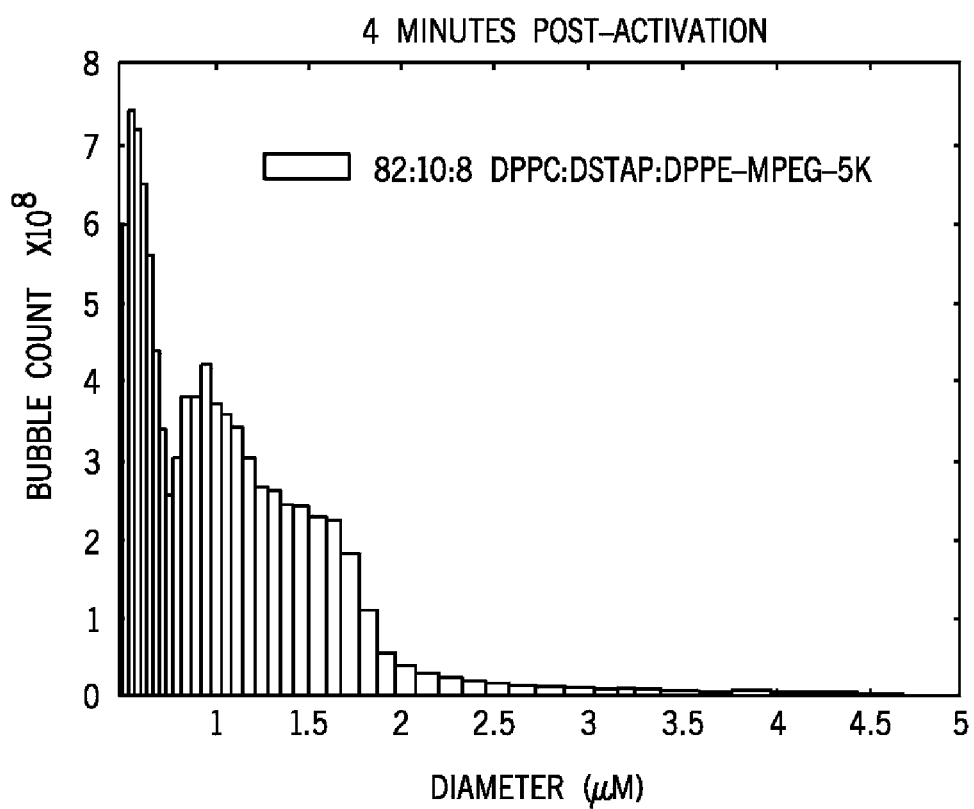
FIG. 14 graphically illustrates microbubble sizing data for the 82 mole percent DPPC, 10 mole percent DSTAP, and 8 mole percent DPPE-MPEG-5K formulation at four (4) minutes post activation.
Figure 15:
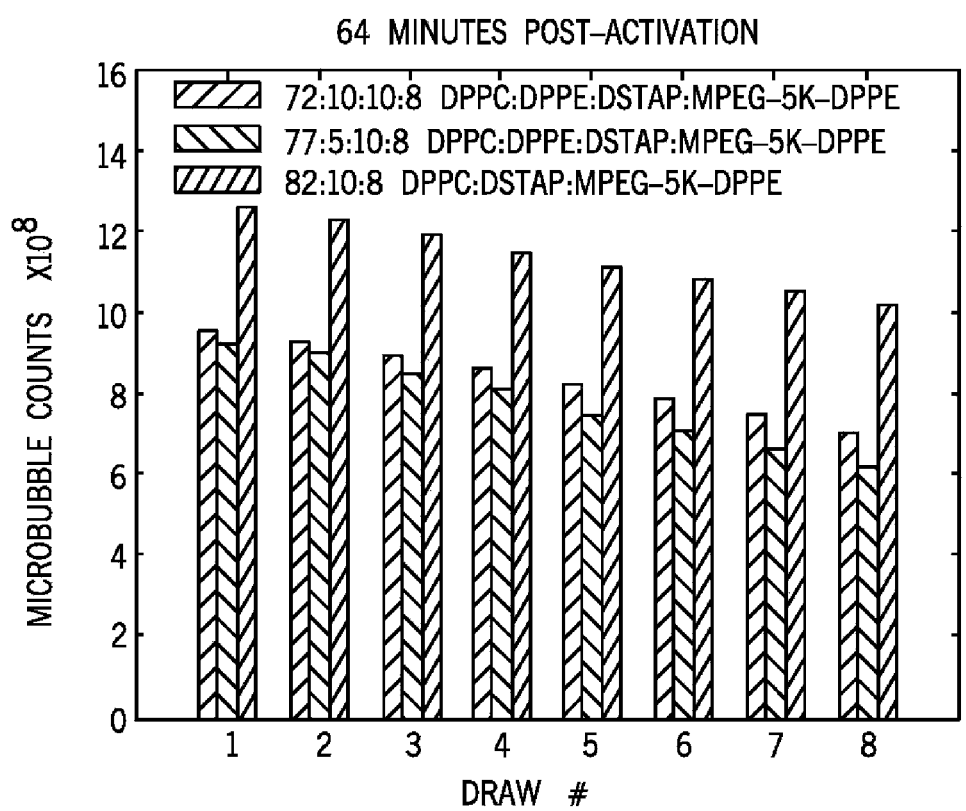
FIG. 15 graphically illustrates microbubble counts for each of the formulations recited versus Draw# at sixty-four (64) minutes post activation.
Figure 16:
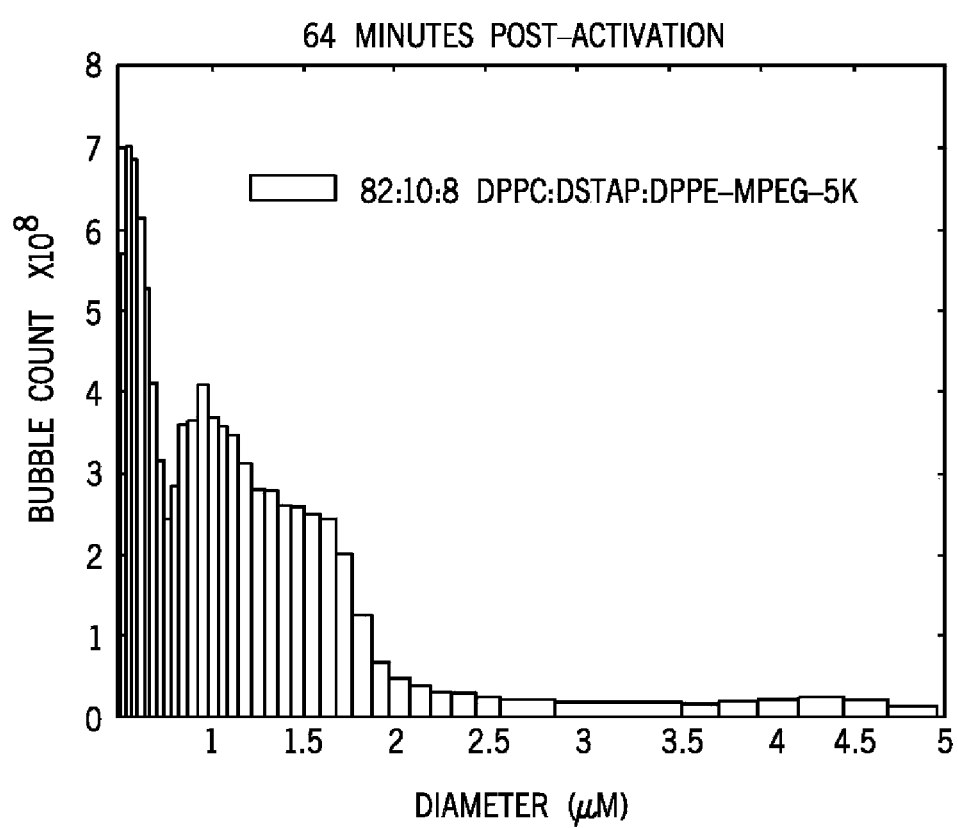
FIG. 16 graphically illustrates microbubble sizing data for the 82 mole percent DPPC, 10 mole percent DSTAP, and 8 mole percent DPPE-MPEG-5K formulation at sixty-four (64) minutes post activation.

As shown in FIG. 12, Definity causes much more delayed renal enhancement than MVT-100 (Mb-neutr).

Example 6

Echocardiography was performed in 5 pigs. Animals were injected randomly with either Definity or MVT-100. Ultrasound parameters were frequency=2 MHz, MI=0.18 or 0.35. Each vial was mixed in a 100 ml bag of saline. Approximate volume in each vial was 1.5-1.6 ml. All were infused at a rate of 3.6 to ~5.0 mL per minute. Pig weights were ~27-30 kg.

Assuming 1.5 ml microbubbles/100 ml=15 uLMB/ml solution×3.6 mL/min=54 uL/min; divided by 30 kg=1.8 uL/kg/min. Images were assessed by the operators for contrast enhancement of the heart chambers and myocardium. Animals were monitored for blood pressure, heart rate and paO$_2$. Image contrast was judged to be comparable from MVT-100 and Definity. There was no change in heart rate, blood pressure or paO$_2$ after injection of either agent. Imaging was comparable with both MVT-100 and Definity.

Example 7

Cationic Lipid Use

A lipid blend was prepared as in Example 1, comprising a cationic lipid 1,2-Distearoyl-3-trimethylammonium-propane chloride 9 (DSTAP) in combination with, inter alia, a cone-shaped neutral lipid MPEG-5K-DPPE.

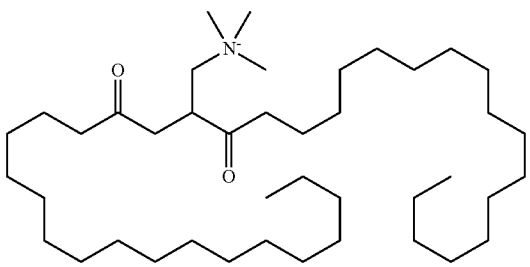

Table 10 summarizes particle size data for three (3) compositions at two time points, namely four (4) minutes post-activation and 64 minutes post-activation.

TABLE 10

| SampleD | Post-Act Time (min) | Mean Num Wt | Mean Vol Wt | 0.51-10 μm Counts | 0.51-10 μm % | 10-25 μm Counts | 10-25 μm % | >25 μm Counts | >25 μm % |
|---|---|---|---|---|---|---|---|---|---|
| 72:10:10:8 DPPC:DPPE:DSTAP:MPEG-5K-DPPE | 4 | 0.96 | 13.79 | 8.12E+09 | 99.9914 | 6.67E+05 | 0.0082 | 1.30E+05 | 0.0016 |
| 72:10:10:8 DPPC:DPPE:DSTAP:MPEG-5K-DPPE | 64 | 1.06 | 17.09 | 7.37E+09 | 99.9440 | 5.26E+06 | 0.0713 | 1.16E+05 | 0.0016 |
| 77:5:10:8 DPPC:DPPE:DSTAP:MPEG-5K-DPPE | 4 | 0.93 | 156.32 | 8.08E+09 | 99.9912 | 6.81E+05 | 0.0084 | 1.30E+05 | 0.0016 |
| 77:5:10:8 DPPC:DPPE:DSTAP:MPEG-5K-DPPE | 64 | 1.01 | 33.80 | 7.10E+09 | 99.9725 | 2.38E+06 | 0.0335 | 2.03E+05 | 0.0029 |
| 82:10:8 DPPC:DSTAP:MPEG-5K-DPPE | 4 | 0.91 | 15.13 | 9.75E+09 | 99.9948 | 4.20E+05 | 0.0043 | 1.16E+05 | 0.0012 |
| 82:10:8 DPPC:DSTAP:MPEG-5K-DPPE | 64 | 1.02 | 28.18 | 9.79E+09 | 99.9201 | 8.30E+06 | 0.0847 | 9.86E+05 | 0.0101 |
| SALINE | N/A | 0.89 | 32.89 | 1.94E+07 | 99.7017 | 4.35E+04 | 0.2237 | 4.35E+04 | 0.2237 |

FIG. 12 graphically illustrates total microbubble counts measured for the three formulations listed in Table 10+a formulation containing 62 mol % DPPC, 10 mol % DPPE, 20 mol % DSTAP, and 8 mol % DPPE-MPEG-5K. Referring to Table 10. The formulation comprising 82 mole percent of DPPC, 10 mole percent DSTAP, and 8 mole percent MPEG-5K-DPPE showed the greater number of microbubbles at both four (4) minutes post activation and sixty-four (64) minutes post-activation.

Prophetic Example 8

Thousands of patients are administered Applicant's microbubble composition described above in Example 1. Compared to clinical use of DEFINITY, the incidence of back pain is less using Applicant's microbubble composition of Example 2.

Prophetic Example 9

A stability study is performed at room temperature. HPLC is used to monitor the break-down of the lipids. Samples are periodically agitated on the VialMix to produce microbubbles. The numbers of microbubbles and size are studied by a particle sizing system. Applicant's microbubble composition of Example 2 has a longer shelf-life at room temperature than DEFINITY, also as confirmed in Example 4.

Prophetic Example 10

DPPC, DPPE-PEG(5000) and DPPE in the same ratios as Example 3 are dissolved in chloroform and agitated and heated until dissolved in a round bottom flask. The chloroform is evaporated under heat and reduced pressure leaving a dry film of lipids. The lipids are rehydrated in a mixture of water containing Macrogol 4000. The material is agitated until the lipids are suspended uniformly. The suspension is placed into vials and lyophilized. The vials contain a dried cake of lipid with PEG filled with head space of perfluorobutane (PFB) gas and nitrogen (65% PFB/35% nitrogen). The vials are sealed and heated to 38° C. for 4 hours. For clinical imaging use, the microbubbles are prepared by injecting normal saline into the vials and gentle agitation by hand.

Prophetic Example 11

Example 2 is substantially repeated except that one-tenth of the DPPE-PEG(5000) is replaced by DPPE-PEG(5000)-Folate. The resulting lipid suspension contains 0.75 mg lipid blend (consisting of 0.046 mg DPPE, 0.400 mg DPPC, and 0.274 mg MPEG5000 DPPE) and 0.030 mg DPPE (PEG5000) Folate. The lipid suspension is then useful for making microbubbles to target cells, e.g. cancers, over expressing the folate receptor. Compared to microbubbles containing phosphatidic acid, microbubbles prepared with the above formulation containing DPPE have improved targeting and cellular uptake.

Prophetic Example 12

The lipids used in Example 2 are used to emulsify perfluoropentane. The final concentration of perfluoropentane is 2% w/vol and the lipids are 3 mg/ml. The chilled material is transferred into vials and the head space of air is removed from the vials by negative pressure. The vials are sealed. To produce microbubbles the sealed vials are then agitated on a VialMix as described in Example 2.

Prophetic Example 13

An emulsion of perfluoropentane is prepared using DPPC/DPPE-PEG(5,000)/DPPE by homogenizing the lipids with DDFP by high pressure homogenization under elevated pressure at 4° C. The resulting emulsion had 2% w/vol DDFP and 0.3% w/vol lipid. A similar emulsion is prepared with DPPC/DPPE-PEG without DPPE. Samples are stored in sealed vials at room temperature. Particle sizing shows increased particle count and better maintenance of particle size for the formulation containing DPPE.

While the preferred embodiments of the present invention have been illustrated in detail, it should be apparent that modifications and adaptations to those embodiments may occur to one skilled in the art without departing from the scope of the present invention as set forth herein.

We claim:

1. A composition for stabilizing an octafluoropropane emulsion, comprising:
   octafluoropropane;
   phosphatidylcholine;
   phosphatidylethanolamine-polyethylene glycol (PEG); and
   dipalmitoylphosphatidylethanolamine (DPPE),
   wherein
   the composition comprises no dipalmitoylphosphatidic acid (DPPA),
   the composition has a pH between 6.2 and 6.8, and
   the dipalmitoylphosphatidylethanolamine (DPPE) is at a concentration between about 5 and about 20 mole percent of the composition.

2. The composition of claim 1, wherein the dipalmitoylphosphatidylethanolamine (DPPE) is at a concentration about 10 mole percent of the composition.

3. The composition of claim 1, comprising: about 82 mole percent phosphatidylcholine; about 8 mole percent phosphatidylethanolamine-PEG; and about 10 mole percent dipalmitoylphosphatidylethanolamine (DPPE).

4. The composition of claim 3, comprising: about 82 mole percent dipalmitoylphosphatidylcholine(DPPC); about 8 mole percent dipalmitoylphosphatidylethanolamine-PEG(5,000)(DPPE-PEG(5,000)); and about 10 mole percent dipalmitoylphosphatidylethanolamine(DPPE).

5. The composition of claim 1, wherein the phosphatidylcholine, the phosphatidylethanolamine-PEG, and dipalmitoylphosphatidylethanolamine(DPPE), comprise an aggregate concentration from about 0.75 mg/ml to about 1.5 mg/ml.

6. The composition of claim 5, further comprising: a bifunctional PEG'ylated moiety of DPPE-PEG; wherein the bifunctional PEG'ylated moiety of DPPE-PEG is present in an amount ranging from about 1 mole percent to about 20 mole percent of the total PEG'ylated lipid.

7. The composition of claim 5, further comprising:
   propylene glycol;
   glycerol; and
   saline.

8. A lyophilized composition, comprising:
   octafluoropropane;
   phosphatidylcholine;
   phosphatidylethanolamine-polyethylene glycol (PEG); and
   dipalmitoylphosphatidylethanolamine (DPPE),
   wherein
   the composition comprises no dipalmitoylphosphatidic acid (DPPA),
   the composition has a pH between 6.2 and 6.8, and
   the dipalmitoylphosphatidylethanolamine (DPPE) is at a concentration between about 5 and about 20 mole percent of the composition.

9. The composition of claim 8, comprising: about 82 mole percent dipalmitoylphosphatidylcholine(DPPC); about 8 mole percent dipalmitoylphosphatidylethanolamine-PEG(5,000)(DPPE-PEG(5,000)); and about 10 mole percent dipalmitoylphosphatidylethanolamine (DPPE).

10. A composition of an octafluoropropane emulsion, comprising:
    octafluoropropane;
    phosphatidylcholine;
    phosphatidylethanolamine-polyethylene glycol (PEG); and
    dipalmitoylphosphatidylethanolamine (DPPE),
    wherein
    the composition comprises no dipalmitoylphosphatidic acid (DPPA),
    the composition has a pH between 6.2 and 6.8, and
    the dipalmitoylphosphatidylethanolamine (DPPE) is at a concentration between about 5 and about 20 mole percent of the composition.

11. The composition of claim 10, wherein the octafluoropropane is encapsulated in phospholipid coated microspheres having a mean particle size of 1.1 µm to 3.3 µm, with 98% less than 10 µm, and a maximum diameter of 20 µm.

12. The composition of claim 11, wherein the phosphatidylcholine, the phosphatidylethanolamine-PEG, and dipalmitoylphosphatidylethanolamine (DPPE), comprise an aggregate concentration from about 0.75 mg/ml to about 1.5 mg/ml.

* * * * *